US012565658B2

(12) United States Patent
Xue et al.

(10) Patent No.: US 12,565,658 B2
(45) Date of Patent: Mar. 3, 2026

(54) CD33 TARGETED CHIMERIC ANTIGEN RECEPTOR MODIFIED T CELLS FOR TREATMENT OF CD33 POSITIVE MALIGNANCIES

(71) Applicant: City of Hope, Duarte, CA (US)

(72) Inventors: Tongyuan Xue, Duarte, CA (US); David A. Horne, Duarte, CA (US); Lihua Elizabeth Budde, Duarte, CA (US); Stephen Forman, Duarte, CA (US); Marissa M. Del Real, Duarte, CA (US)

(73) Assignee: City of Hope, Duarte, CA (US)

( * ) Notice: Subject to any disclaimer, the term of this patent is extended or adjusted under 35 U.S.C. 154(b) by 954 days.

(21) Appl. No.: 17/614,233

(22) PCT Filed: Jun. 1, 2020

(86) PCT No.: PCT/US2020/035579
§ 371 (c)(1),
(2) Date: Nov. 24, 2021

(87) PCT Pub. No.: WO2020/243713
PCT Pub. Date: Dec. 3, 2020

(65) Prior Publication Data
US 2022/0213489 A1 Jul. 7, 2022

Related U.S. Application Data

(60) Provisional application No. 62/855,906, filed on May 31, 2019.

(51) Int. Cl.
*C12N 15/62* (2006.01)
*C07K 14/725* (2006.01)

(52) U.S. Cl.
CPC .......... *C12N 15/62* (2013.01); *C07K 14/7051* (2013.01)

(58) Field of Classification Search
None
See application file for complete search history.

(56) References Cited

U.S. PATENT DOCUMENTS 9,944,702 B2 4/2018 Galetto
2017/0145094 A1 5/2017 Galetto

FOREIGN PATENT DOCUMENTS

| CN | 104877032 | | 9/2015 |
| CN | 105384823 | | 3/2016 |
| CN | 105384823 A | * | 3/2016 |
| CN | 107267619 | | 10/2017 |
| CN | 107353343 | | 11/2017 |
| WO | WO 2017/015490 | | 1/2017 |
| WO | WO 2017/062604 | | 4/2017 |
| WO | WO 2018/075989 | | 4/2018 |
| WO | WO 2018/213337 | | 11/2018 |
| WO | WO 2019/178382 | | 9/2019 |

OTHER PUBLICATIONS

Andrews et al., "Precursors of colony-forming cells in humans can be distinguished from colony-forming cells by expression of the CD33 and CD34 antigens and light scatter properties," J Exp Med., 1989, 169:1721-1731.
Budde et al., "Remissions of Acute Myeloid Leukemia and Blastic Plasmacytoid Dendritic Cell Neoplasm Following Treatment with CD123-Specific CAR T Cells: A First-in-Human Clinical Trial," Blood, Dec. 7, 2017, 130(Supplement 1):811.
Dohner et al., "Acute Myeloid Leukemia," N Engl J Med., 2015, 373:1136-1152.
Ehninger et al., "Distribution and levels of cell surface expression of CD33 and CD123 in acute myeloid leukemia," Blood Cancer, 2014, 4:e218.
Elliot et al., "Human Tumor-Infiltrating Myeloid Cells: Phenotypic and Functional Diversity," Front Immunol., 2017, 8:86.
International Preliminary Report on Patentability in International Application No. PCT/US2020/035579, dated Nov. 16, 2021, 10 pages.
International Search Report and Written Opinion in International Application No. PCT/US2020/035579, dated Dec. 7, 2020, 19 pages.
Invitation to Pay Fees in International Application No. PCT/US2020/035579, dated Oct. 16, 2020, 31 pages.
Priceman et al., "Co-stimulatory signaling determines tumor antigen sensitivity and persistence of CAR T cells targeting PSCA+ metastatic prostate cancer," Oncoimmunology, 2018, 7(2):e1380764.
Schneider et al., "A Unique Human Immunoglobulin Heavy Chain Variable Domain-Only CD33 Car for the Treatment of Acute Myeloid Leukemia," Frontiers in Oncology, Nov. 22, 2018, 8:539.
Schuster et al., "Chimeric Antigen Receptor T Cells in Refractory B-Cell Lymphomas," N Engl J Med., Dec. 28, 2017, 377:2545-2554.
Walter et al., "Acute myeloid leukemia stem cells and CD33-targeted immunotherapy," Blood, 2012, 119:6198-6208.
Walter, "Expanding use of CD33-directed immunotherapy," Expert Opinion on Biological Therapy, Jul. 2020, 20(9):955-958.

* cited by examiner

*Primary Examiner* — Valarie E Bertoglio
*Assistant Examiner* — Risa Takenaka
(74) *Attorney, Agent, or Firm* — Fish & Richardson P.C.

(57) ABSTRACT

Chimeric antigen receptors targeted to CD33 are described together with their use in treating various cancers and in reducing myeloid derived suppressor cells in a patient.

7 Claims, 21 Drawing Sheets
Specification includes a Sequence Listing.

CD33CAR: huCD33scFv-CD8h-CD8tm-41BB-CD3ζ-T2A-EGFRt_epHIV7

QVQLVQSGAEVKKPGSSVKVSCKASGYTFTDYNMHWVRQAPGQGLEWIGYIYPYN
GGTGYNQKFKSKATITADESTNTAYMELSSLRSEDTAVYYCARGRPAMDYWGQGT
LVTVSSGGGGSGGGGSGGGGSDIQMTQSPSSLSASVGDRVTITCRASESVDNYGI
SFMNWFQQKPGKAPKLLIYAASNQGSGVPSRFSGSGSGTDFTLTISSLQPDDFAT
YYCQQSKEVPWTFGQGTKVEIKTTTPAPRPPTPAPTIASQPLSLRPEACRPAAGG
AVHTRGLDFACDIYIWAPLAGTCGVLLLSLVITLYCKRGRKKLLYIFKQPFMRPV
QTTQEEDGCSCRFPEEEEGGCELGGGRVKFSRSADAPAYQQGQNQLYNELNLGRR
EEYDVLDKRRGRDPEMGGKPRRKNPQEGLYNELQKDKMAEAYSEIGMKGERRRGK
GHDGLYQGLSTATKDTYDALHMQALPPR

CD33scFv-CD8h-CD8tm-41BB-g3(op)-Zeta

FIG. 14A

QVQLVQSGAEVKKPGSSVKVSCKASGYTFTDYNMHWVRQAPGQGLEWIGYIYPYN
GGTGYNQKFKSKATITADESTNTAYMELSSLRSEDTAVYYCARGRPAMDYWGQGT
LVTVSSGGGGSGGGGSGGGGSDIQMTQSPSSLSASVGDRVTITCRASESVDNYGI
SFMNWFQQKPGKAPKLLIYAASNQGSGVPSRFSGSGSGTDFTLTISSLQPDDFAT
YYCQQSKEVPWTFGQGTKVEIKESKYGPPCPPCPAPEFEGGPSVFLFPPKPKDTL
MISRTPEVTCVVVDVSQEDPEVQFNWYVDGVEVHNAKTKPREEQFQSTYRVVSVL
TVLHQDWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLTVDKSR
WQEGNVFSCSVMHEALHNHYTQKSLSLSLGKMALIVLGGVAGLLLFIGLGIFFKR
GRKKLLYIFKQPFMRPVQTTQEEDGCSCRFPEEEEGGCELGGGRVKFSRSADAPA
YQQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR

CD33scFv-IgG4(S228P,L235E,N297Q)-CD4tm-41BB(op)-g3-Zeta

*FIG. 14B*

CD33scFvop-CD8h-CD8tm-41BBop-Zetaop-T2A-EGFRt

```
                                                    M  L  L  L  V  T  S  ·
2041                                                ATGCTGCTCC TTGTCACATC

· L  L  L  C  E  L  P  H  P  A  F  L  L  I  P  Q  V  Q  L  V ·
2101 CCTGCTGCTG TGCGAACTGC CACATCCCGC CTTCCTGCTG ATCCCCCAAG TGCAGCTCGT

· Q  S  G  A  E  V  K  K  P  G  S  S  V  K  V  S  C  K  A  S ·
2161 GCAGTCCGGA GCCGAAGTCA AGAAGCCTGG CAGCTCCGTC AAGGTGTCCT GCAAAGCCTC

· G  Y  T  F  T  D  Y  N  M  H  W  V  R  Q  A  P  G  Q  G  L ·
2221 CGGCTACACC TTTACCGACT ACAACATGCA CTGGGTCCGC CAAGCACCTG GACAGGGACT

· E  W  I  G  Y  I  Y  P  Y  N  G  G  T  G  Y  N  Q  K  F  K ·
2281 GGAGTGGATT GGGTACATCT ACCCTTACAA CGGAGGCACC GGGTACAACC AGAAGTTCAA

· S  K  A  T  I  T  A  D  E  S  T  N  T  A  Y  M  E  L  S  S ·
2341 GTCGAAGGCC ACCATTACCG CGGACGAATC CACCAACACC GCGTATATGG AGCTCTCATC

· L  R  S  E  D  T  A  V  Y  Y  C  A  R  G  R  P  A  M  D  Y ·
2401 CTTGCGGTCG GAGGACACTG CCGTGTACTA CTGCGCGAGG GGTAGACCGG CAATGGACTA

· W  G  Q  G  T  L  V  T  V  S  S  G  G  G  G  S  G  G  G  G ·
2461 CTGGGGCCAG GGCACTCTCG TCACCGTGTC CTCTGGTGGT GGAGGCTCAG GAGGAGGGGG

· S  G  G  G  G  S  D  I  Q  M  T  Q  S  P  S  S  L  S  A  S ·
2521 ATCCGGTGGA GGAGGGAGCG ATATCCAGAT GACGCAGTCA CCCTCGTCCC TGAGCGCTTC

· V  G  D  R  V  T  I  T  C  R  A  S  E  S  V  D  N  Y  G  I ·
2581 CGTGGGCGAT CGCGTGACTA TCACTTGCCG GGCTTCCGAG TCCGTGGATA ACTACGGAAT

· S  F  M  N  W  F  Q  Q  K  P  G  K  A  P  K  L  L  I  Y  A ·
2641 TTCCTTTATG AACTGGTTCC AGCAAAAGCC GGGAAAGGCC CCAAAGCTCC TGATCTACGC

· A  S  N  Q  G  S  G  V  P  S  R  F  S  G  S  G  S  G  T  D ·
2701 CGCCAGCAAT CAGGGATCGG GAGTGCCCTC ACGGTTCTCC GGGAGCGGTT CAGGCACCGA

· F  T  L  T  I  S  S  L  Q  P  D  D  F  A  T  Y  Y  C  Q  Q ·
2761 CTTCACCCTT ACTATTTCGA GCCTGCAACC TGACGATTTC GCCACTTATT ACTGCCAACA

· S  K  E  V  P  W  T  F  G  Q  G  T  K  V  E  I  K  T  T  T ·
2821 GTCCAAGGAA GTGCCGTGGA CGTTCGGCCA GGGGACCAAG GTGGAAATCA AG ACCACGAC

· P  A  P  R  P  P  T  P  A  P  T  I  A  S  Q  P  L  S  L  R ·
2881 GCCAGCGCCG CGACCACCAA CACCGGCGCC CACCATCGCG TCGCAGCCCC TGTCCCTGCG

· P  E  A  C  R  P  A  A  G  G  A  V  H  T  R  G  L  D  F  A ·
2941 CCCAGAGGCG TGCCGGCCAG CGGCGGGGGG CGCAGTGCAC ACGAGGGGGC TGGACTTCGC

· C  D  I  Y  I  W  A  P  L  A  G  T  C  G  V  L  L  L  S  L ·
3001 CTGTGATATC TACATCTGGG CGCCCTTGGC CGGGACTTGT GGGGTCCTTC TCCTGTCACT

· V  I  T  L  Y  C  K  R  G  R  K  K  L  L  Y  I  F  K  Q  P ·
3061 GGTTATCACC CTTTACTGC A AGCGGGGCAG AAAGAAGCTG CTGTACATCT TCAAGCAGCC

· F  M  R  P  V  Q  T  T  Q  E  E  D  G  C  S  C  R  F  P  E ·
3121 CTTCATGCGG CCCGTGCAGA CCACCCAGGA AGAGGACGGC TGCAGCTGCC GGTTCCCCGA

· E  E  E  G  G  C  E  L  G  G  G  R  V  K  F  S  R  S  A  D
3181 GGAAGAGGAA GGCGGCTGCG AGCTGGGAGG CGGCAGAGTG AAGTTCAGCC GGTCCGCCGA
```

*FIG. 15A*

```
       ·A   P   A    Y   Q   Q   G    Q   N   Q    L   Y   N    E   L   N    L    G   R   R·
3241   CGCCCCTGCC TACCAGCAGG GCCAGAACCA GCTGTACAAC GAGCTGAACC TGGGCAGGCG

·E   E   Y    D   V   L   D    K   R   R    G   R   D    P   E   M    G    G   K   P·
3301   GGAGGAATAC GACGTGCTGG ACAAGCGGAG AGGCCGGGAC CCTGAGATGG GCGGCAAGCC

·R   R   K    N   P   Q   E    G   L   Y    N   E   L    Q   K   D    K    M   A   E·
3361   CAGGCGGAAG AACCCTCAGG AAGGCCTGTA TAACGAACTG CAGAAAGACA AGATGGCCGA

·A   Y   S    E   I   G   M    K   G   E    R   R   R    G   K   G    H    D   G   L·
3421   GGCCTACAGC GAGATCGGCA TGAAGGGCGA GCGGCGGAGG GGCAAGGGCC ACGACGGCCT

·Y   Q   G    L   S   T   A    T   K   D    T   Y   D    A   L   H    M    Q   A   L·
3481   GTACCAGGGC CTGAGCACCG CCACCAAGGA TACCTACGAC GCCCTGCACA TGCAGGCCCT

·P   P   R    L   E   G   G    E   G   R    G   S   L    L   T   C    G    D   V·
3541   GCCCCCAAGG CTCGAGGGCG GCGGAGAGGG CAGAGGAAGT CTTCTAACAT GCGGTGACGT

·E   E   N    P   G   P   R    M   L   L    L   V   T    S   L   L    L    C   E   L·
3601   GGAGGAGAAT CCCGGCCCTA GGATGCTTCT CCTGGTGACA AGCCTTCTGC TCTGTGAGTT

·P   H   P    A   F   L   L    I   P   R    K   V   C    N   G   I    G    I   G   E·
3661   ACCACACCCA GCATTCCTCC TGATCCCACG CAAAGTGTGT AACGGAATAG GTATTGGTGA

·F   K   D    S   L   S   I    N   A   T    N   I   K    H   F   K    N    C   T   S·
3721   ATTTAAAGAC TCACTCTCCA TAAATGCTAC GAATATTAAA CACTTCAAAA ACTGCACCTC

·I   S   G    D   L   H   I    L   P   V    A   F   R    G   D   S    F    T   H   T·
3781   CATCAGTGGC GATCTCCACA TCCTGCCGGT GGCATTTAGG GGTGACTCCT TCACACATAC

·P   P   L    D   P   Q   E    L   D   I    L   K   T    V   K   E    I    T   G   F·
3841   TCCTCCTCTG GATCCACAGG AACTGGATAT TCTGAAAACC GTAAAGGAAA TCACAGGGTT

·L   L   I    Q   A   W   P    E   N   R    T   D   L    H   A   F    E    N   L   E·
3901   TTTGCTGATT CAGGCTTGGC CTGAAAACAG GACGGACCTC CATGCCTTTG AGAACCTAGA

·I   I   R    G   R   T   K    Q   H   G    Q   F   S    L   A   V    V    S   L   N·
3961   AATCATACGC GGCAGGACCA AGCAACATGG TCAGTTTTCT CTTGCAGTCG TCAGCCTGAA

·I   T   S    L   G   L   R    S   L   K    E   I   S    D   G   D    V    I   I   S·
4021   CATAACATCC TTGGGATTAC GCTCCCTCAA GGAGATAAGT GATGGAGATG TGATAATTTC

·G   N   K    N   L   C   Y    A   N   T    I   N   W    K   K   L    F    G   T   S·
4081   AGGAAACAAA AATTTGTGCT ATGCAAATAC AATAAACTGG AAAAAACTGT TTGGGACCTC

·G   Q   K    T   K   I   I    S   N   R    G   E   N    S   C   K    A    T   G   Q·
4141   CGGTCAGAAA ACCAAAATTA TAAGCAACAG AGGTGAAAAC AGCTGCAAGG CCACAGGCCA

·V   C   H    A   L   C   S    P   E   G    C   W   G    P   E   P    R    D   C   V·
4201   GGTCTGCCAT GCCTTGTGCT CCCCCGAGGG CTGCTGGGGC CCGGAGCCCA GGGACTGCGT

·S   C   R    N   V   S   R    G   R   E    C   V   D    K   C   N    L    L   E   G·
4261   CTCTTGCCGG AATGTCAGCC GAGGCAGGGA ATGCGTGGAC AAGTGCAACC TTCTGGAGGG

·E   P   R    E   F   V   E    N   S   E    C   I   Q    C   H   P    E    C   L   P·
4321   TGAGCCAAGG GAGTTTGTGG AGAACTCTGA GTGCATACAG TGCCACCCAG AGTGCCTGCC

·Q   A   M    N   I   T   C    T   G   R    G   P   D    N   C   I    Q    C   A   H·
4381   TCAGGCCATG AACATCACCT GCACAGGACG GGGACCAGAC AACTGTATCC AGTGTGCCCA
```

*FIG. 15B*

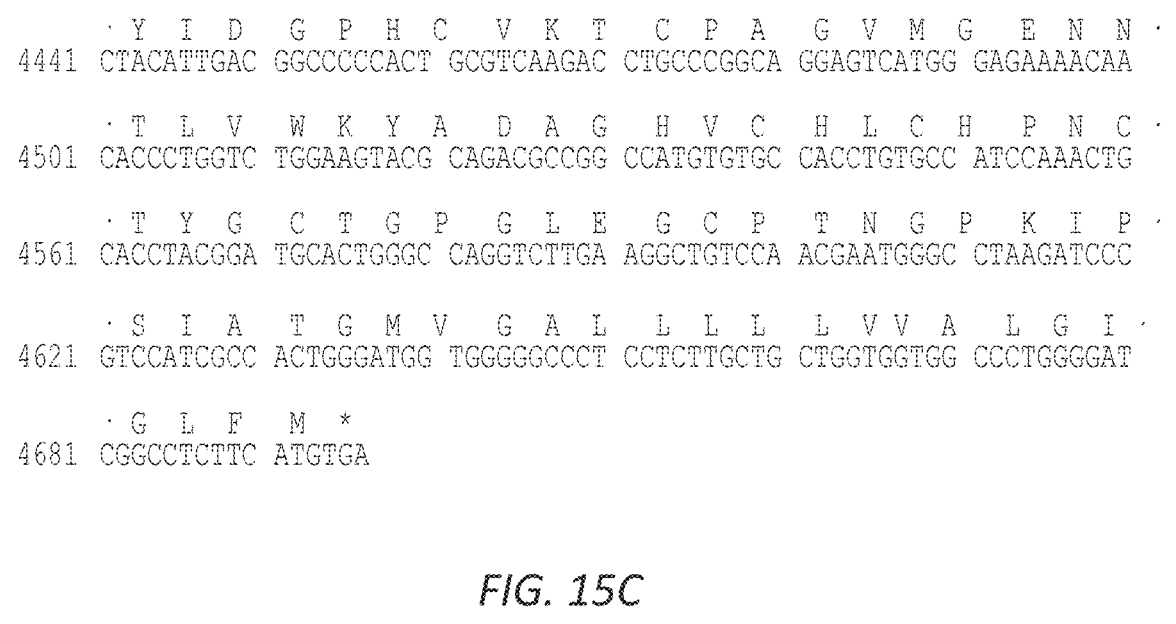

```
      · Y   I   D    G   P   H    C   V   K    T   C   P    A   G   V    M   G   E    N   N ·
4441  CTACATTGAC  GGCCCCCACT  GCGTCAAGAC  CTGCCCGGCA  GGAGTCATGG  GAGAAAACAA

· T   L   V    W   K   Y    A   D   A    G   H   V    C   H   L    C   H   P    N   C ·
4501  CACCCTGGTC  TGGAAGTACG  CAGACGCCGG  CCATGTGTGC  CACCTGTGCC  ATCCAAACTG

· T   Y   G    C   T   G    P   G   L    E   G   C    P   T   N    G   P   K    I   P ·
4561  CACCTACGGA  TGCACTGGGC  CAGGTCTTGA  AGGCTGTCCA  ACGAATGGGC  CTAAGATCCC

· S   I   A    T   G   M    V   G   A    L   L   L    L   L   V    V   A   L    G   I ·
4621  GTCCATCGCC  ACTGGGATGG  TGGGGGCCCT  CCTCTTGCTG  CTGGTGGTGG  CCCTGGGGAT

· G   L   F    M   *
4681  CGGCCTCTTC  ATGTGA
```

FIG. 15C

CD33scFv-IgG4(L235E,N27Q)-41BB-Zeta(CO)-T2A-EGFRt

```
                                              M   L   L   V   T   S ·
2041                                         ATGCTGCTCC TTGTCACATC

· L   L   L   C   E   L   P   H   P   A   F   L   L   I   P   Q   V   Q   L   V ·
2101 CCTGCTGCTG TGCGAACTGC CACATCCCGC CTTCCTGCTG ATCCCCCAAG TGCAGCTCGT

· Q   S   G   A   E   V   K   P   G   S   S   V   K   V   S   C   K   A   S ·
2161 GCAGTCCGGA GCCGAAGTCA AGAAGCCTGG CAGCTCCGTC AAGGTGTCCT GCAAAGCCTC

· G   Y   T   F   T   D   Y   N   M   H   W   V   R   Q   A   P   G   Q   G   L ·
2221 CGGCTACACC TTTACCGACT ACAACATGCA CTGGGTCCGC CAAGCACCTG GACAGGGACT

· E   W   I   G   Y   I   Y   P   Y   N   G   G   T   G   Y   N   Q   K   F   K ·
2281 GGAGTGGATT GGGTACATCT ACCCTTACAA CGGAGGCACC GGGTACAACC AGAAGTTCAA

· S   K   A   T   I   T   A   D   E   S   T   N   T   A   Y   M   E   L   S   S ·
2341 GTCGAAGGCC ACCATTACCG CGGACGAATC CACCAACACC GCGTATATGG AGCTCTCATC

· L   R   S   E   D   T   A   V   Y   Y   C   A   R   G   R   P   A   M   D   Y ·
2401 CTTGCGGTCG GAGGACACTG CCGTGTACTA CTGCGCGAGG GGTAGACCGG CAATGGACTA

· W   G   Q   G   T   L   V   T   V   S   S   G   G   G   G   S   G   G   G ·
2461 CTGGGGCCAG GGCACTCTCG TCACCGTGTC CTCTGGTGGT GGAGGCTCAG GAGGAGGGGG

· S   G   G   G   G   S   D   I   Q   M   T   Q   S   P   S   S   L   S   A   S ·
2521 ATCCGGTGGA GGAGGGAGCG ATATCCAGAT GACGCAGTCA CCCTCGTCCC TGAGCGCTTC

· V   G   D   R   V   T   I   T   C   R   A   S   E   S   V   D   N   Y   G   I ·
2581 CGTGGGCGAT CGCGTGACTA TCACTTGCCG GGCTTCCGAG TCCGTGGATA ACTACGGAAT

· S   F   M   N   W   F   Q   Q   K   P   G   K   A   P   K   L   L   I   Y   A ·
2641 TTCCTTTATG AACTGGTTCC AGCAAAAGCC GGGAAAGGCC CCAAAGCTCC TGATCTACGC

· A   S   N   Q   G   S   G   V   P   S   R   F   S   G   S   G   S   G   T   D ·
2701 CGCCAGCAAT CAGGGATCGG GAGTGCCCTC ACGGTTCTCC GGGAGCGGTT CAGGCACCGA

· F   T   L   T   I   S   S   L   Q   P   D   D   F   A   T   Y   Y   C   Q   Q ·
2761 CTTCACCCTT ACTATTTCGA GCCTGCAACC TGACGATTTC GCCACTTATT ACTGCCAACA

· S   K   E   V   P   W   T   F   G   Q   G   T   K   V   E   I   K   E   S   K ·
2821 GTCCAAGGAA GTGCCGTGGA CGTTCGGCCA GGGGACCAAG GTGGAAATCA AGGAGAGCAA

· Y   G   P   P   C   P   P   C   P   A   P   E   F   E   G   G   P   S   V   F ·
2881 ATACGGACCG CCGTGTCCAC CTGTCCTGC ACCCGAGTTC GAAGGCGGCC CTTCCGTGTT

· L   F   P   P   K   P   K   D   T   L   M   I   S   R   T   P   E   V   T   C ·
2941 CCTGTTCCCG CCGAAGCCCA AGGACACCCT GATGATCTCG AGAACCCCGG AGGTGACCTG

· V   V   V   D   V   S   Q   E   D   P   E   V   Q   F   N   W   Y   V   D   G ·
3001 CGTGGTGGTG GACGTGTCCC AGGAAGATCC CGAGGTCCAG TTCAATTGGT ACGTGGACGG

· V   E   V   H   N   A   K   T   K   P   R   E   E   Q   F   Q   S   T   Y   R ·
3061 CGTGGAAGTG CACAATGCCA AGACCAAGCC CAGAGAGGAA CAGTTCCAAA GCACCTACCG
```

*FIG. 15D*

```
         · V   V   S   V   L   T   V   L   H   Q   D   W   L   N   G   K   E   Y   K   C ·
    3121 GGTGGTGTCC GTGCTGACCG TGCTGCACCA GGACTGGCTG AACGGCAAAG AGTACAAGTG

· K   V   S   N   K   G   L   P   S   S   I   E   K   T   I   S   K   A   K   G ·
    3181 CAAGGTGTCC AACAAGGGCC TGCCCAGCAG CATCGAGAAA ACCATCAGCA AGGCCAAGGG

· Q   P   R   E   P   Q   V   Y   T   L   P   P   S   Q   E   E   M   T   K   N ·
    3241 CCAGCCCCGC GAGCCCCAGG TGTACACACT GCCCCCCAGC CAGGAAGAGA TGACCAAGAA

· Q   V   S   L   T   C   L   V   K   G   F   Y   P   S   D   I   A   V   E   W ·
    3301 CCAGGTGTCC CTGACCTGCC TGGTCAAGGG CTTCTACCCC AGCGATATCG CCGTGGAATG

· E   S   N   G   Q   P   E   N   N   Y   K   T   T   P   P   V   L   D   S   D ·
    3361 GGAGAGCAAC GGCCAGCCCG AGAACAACTA CAAGACCACC CCCCCTGTGC TGGACAGCGA

· G   S   F   F   L   Y   S   R   L   T   V   D   K   S   R   W   Q   E   G   N ·
    3421 CGGCAGCTTC TTCCTGTACT CCCGGCTGAC CGTGGACAAG AGCCGGTGGC AGGAAGGCAA

· V   F   S   C   S   V   M   H   E   A   L   H   N   H   Y   T   Q   K   S   L ·
    3481 CGTCTTCAGC TGCAGCGTGA TGCACGAGGC CCTGCACAAC CACTACACCC AGAAGTCTCT

· S   L   S   L   G   K   M   A   L   I   V   L   G   G   V   A   G   L   L   L ·
    3541 GAGCCTGAGC CTGGGCAAGA TGGCCCTGAT CGTGCTGGGC GGAGTGGCCG GACTGCTGCT

· F   I   G   L   G   I   F   F   K   R   G   R   K   K   L   L   Y   I   F   K ·
    3601 GTTTATCGGC CTGGGCATCT TCTTCAAGCG GGGCAGAAAG AAGCTGCTGT ACATCTTCAA

· Q   P   F   M   R   P   V   Q   T   T   Q   E   E   D   G   C   S   C   R   F ·
    3661 GCAGCCCTTC ATGCGGCCCG TGCAGACCAC CCAGGAAGAG GACGGCTGCA GCTGCCGGTT

· P   E   E   E   E   G   G   C   E   L   G   G   G   R   V   K   F   S   R   S ·
    3721 CCCCGAGGAA GAGGAAGGCG GCTGCGAGCT GGGAGGCGGC AGAGTGAAGT TCAGCCGGTC

· A   D   A   P   A   Y   Q   Q   G   Q   N   Q   L   Y   N   E   L   N   L   G ·
    3781 CGCCGACGCC CCTGCCTACC AGCAGGGCCA GAACCAGCTG TACAACGAGC TGAACCTGGG

· R   R   E   E   Y   D   V   L   D   K   R   R   G   R   D   P   E   M   G   G ·
    3841 CAGGCGGGAG GAATACGACG TGCTGGACAA GCGGAGAGGC CGGGACCCTG AGATGGGCGG

· K   P   R   R   K   N   P   Q   E   G   L   Y   N   E   L   Q   K   D   K   M ·
    3901 CAAGCCCAGG CGGAAGAACC CTCAGGAAGG CCTGTATAAC GAACTGCAGA AAGACAAGAT

· A   E   A   Y   S   E   I   G   M   K   G   E   R   R   R   G   K   G   H   D ·
    3961 GGCCGAGGCC TACAGCGAGA TCGGCATGAA GGGCGAGCGG CGGAGGGGCA AGGGCCACGA

· G   L   Y   Q   G   L   S   T   A   T   K   D   T   Y   D   A   L   H   M   Q ·
    4021 CGGCCTGTAC CAGGGCCTGA GCACCGCCAC CAAGGATACC TACGACGCCC TGCACATGCA

· A   L   P   P   R   L   E   G   G   G   E   G   R   G   S   L   L   T   C   G ·
    4081 GGCCCTGCCC CCAAGG CTCG AGGGCGGCGG AGAGGGCAGA GGAAGTCTTC TAACATGCGG

· D   V   E   N   P   G   P   R   M   L   L   L   V   T   S   L   L   L   C ·
    4141 TGACGTGGAG GAGAATCCCG GCCCTAGGAT GCTTCTCCTG GTGACAAGCC TTCTGCTCTG

· E   L   P   H   P   A   F   L   L   I   P   R   K   V   C   N   G   I   G   I ·
    4201 TGAGTTACCA CACCCAGCAT TCCTCCTGAT CCCACGCAAA GTGTGTAACG GAATAGGTAT

· G   E   F   K   D   S   L   S   I   N   A   T   N   I   K   H   F   K   N   C ·
    4261 TGGTGAATTT AAAGACTCAC TCTCCATAAA TGCTACGAAT ATTAAACACT TCAAAAACTG

· T   S   I   S   G   D   L   H   I   L   P   V   A   F   R   G   D   S   F   T ·
    4321 CACCTCCATC AGTGGCGATC TCCACATCCT GCCGGTGGCA TTTAGGGGTG ACTCCTTCAC
```

*FIG. 15E*

```
         ·H   T   P    P   L   D   P    Q   E   L    D   I   L    K   T   V   K    E   I   T·
4381 ACATACTCCT CCTCTGGATC CACAGGAACT GGATATTCTG AAAACCGTAA AGGAAATCAC

·G   F   L    L   I   Q   A    W   P   E    N   R   T    D   L   H    A   F   E   N·
4441 AGGGTTTTTG CTGATTCAGG CTTGGCCTGA AAACAGGACG GACCTCCATG CCTTTGAGAA

·L   E   I    I   R   G   R    T   K   Q    H   G   Q    F   S   L    A   V   V   S·
4501 CCTAGAAATC ATACGCGGCA GGACCAAGCA ACATGGTCAG TTTTCTCTTG CAGTCGTCAG

·L   N   I    T   S   L   G    L   R   S    L   K   E    I   S   D   G    D   V   I·
4561 CCTGAACATA ACATCCTTGG GATTACGCTC CCTCAAGGAG ATAAGTGATG GAGATGTGAT

·I   S   G    N   K   N   L    C   Y   A    N   T   I    N   W   K   K    L   F   G·
4621 AATTTCAGGA AACAAAAATT TGTGCTATGC AAATACAATA AACTGGAAAA AACTGTTTGG

·T   S   G    Q   K   T   K    I   I   S    N   R   G    E   N   S   C    K   A   T·
4681 GACCTCCGGT CAGAAAACCA AAATTATAAG CAACAGAGGT GAAAACAGCT GCAAGGCCAC

·G   Q   V    C   H   A   L    C   S   P    E   G   C    W   G   P   E    P   R   D·
4741 AGGCCAGGTC TGCCATGCCT TGTGCTCCCC CGAGGGCTGC TGGGGCCCGG AGCCCAGGGA

·C   V   S    C   R   N   V    S   R   G    R   E   C    V   D   K   C    N   L   L·
4801 CTGCGTCTCT TGCCGGAATG TCAGCCGAGG CAGGGAATGC GTGGACAAGT GCAACCTTCT

·E   G   E    P   R   E   F    V   E   N    S   E   C    I   Q   C   H    P   E   C·
4861 GGAGGGTGAG CCAAGGGAGT TTGTGGAGAA CTCTGAGTGC ATACAGTGCC ACCCAGAGTG

·L   P   Q    A   M   N   I    T   C   T    G   R   G    P   D   N   C    I   Q   C·
4921 CCTGCCTCAG GCCATGAACA TCACCTGCAC AGGACGGGGA CCAGACAACT GTATCCAGTG

·A   H   Y    I   D   G   P    H   C   V    K   T   C    P   A   G   V    M   G   E·
4981 TGCCCACTAC ATTGACGGCC CCCACTGCGT CAAGACCTGC CCGGCAGGAG TCATGGGAGA

·N   N   T    L   V   W   K    Y   A   D    A   G   H    V   C   H   L    C   H   P·
5041 AAACAACACC CTGGTCTGGA AGTACGCAGA CGCCGGCCAT GTGTGCCACC TGTGCCATCC

·N   C   T    Y   G   C   T    G   P   G    L   E   G    C   P   T   N    G   P   K·
5101 AAACTGCACC TACGGATGCA CTGGGCCAGG TCTTGAAGGC TGTCCAACGA ATGGGCCTAA

·I   P   S    I   A   T   G    M   V   G    A   L   L    L   L   L   V    V   A   L·
5161 GATCCCGTCC ATCGCCACTG GGATGGTGGG GGCCCTCCTC TTGCTGCTGG TGGTGGCCCT

·G   I   G    L   F   M   *
5221 GGGGATCGGC CTCTTCATGT GA
```

*FIG. 15F*

CD33 TARGETED CHIMERIC ANTIGEN RECEPTOR MODIFIED T CELLS FOR TREATMENT OF CD33 POSITIVE MALIGNANCIES

CLAIM OF PRIORITY

This application is a U.S. National Phase Application under 35 U.S.C. § 371 of International Application No. PCT/US2020/035579, filed on Jun. 1, 2020, which claims the benefit of U.S. Provisional Application No. 62/855,906, filed on May 31, 2019. The entire contents of the foregoing are incorporated herein by reference.

SEQUENCE LISTING

The instant application contains a Sequence Listing, which has been submitted electronically in ASCII format and is hereby incorporated by reference in its entirety. Said ASCII copy, created on Nov. 23, 2021, is named Sequence-Listing.txt and is 59,000 bytes in size.

TECHNICAL FIELD

This disclosure concerns leukemia-associated CD33-specific chimeric antigen receptor (CAR)-engineered T cells, methods of formulating, and methods of use as anti-cancer agents selective against CD33-positive cells.

BACKGROUND

Acute myeloid leukemia (AML) is the most common acute leukemia in adults and has the highest mortality rate (Budde et al. (2017) *Blood* 130: 811; Döhner et al. (2015) *N Engl Med* 373:1136-52; Schuster et al. (2017) *N Engl J Med* 377:2545-54). CD33 is expressed on myeloid blasts in 87-98% of AML cases (Ehninger et al. (2014) *Blood Cancer* 4:e218; Andrews R G et al. (1989) *J Exp Med* 169:1721-31). CD33 is also expressed on myeloid-derived suppressor cells (MDSCs), leukemic stem cells (LSCs), and hematopoietic stem cells (HSCs) (Elliot L A et al. (2017) *Front Immunol* 8:86; Walter R B et al. (2012) *Blood* 119:6198-208). The current cure rate for primary AML is 35% and decreases with age; thus, there is an urgent unmet need for novel therapies for AML patients, particularly relapsed or refractory (R/R) AML.

SUMMARY

Described herein are methods for using CD33 targeted CAR T cells (also herein called CD33 CART cells) to treat a variety of cancers, for example, acute myeloid leukemia (AML).

Described herein is a nucleic acid molecule encoding a polypeptide comprising a chimeric antigen receptor (CAR), wherein the CAR comprises an amino acid sequence that is at least 85%, 90%, 95%, 96%, 97%, 98%, 99%, or 100% identical SEQ ID NO: 30 or at least about 85%, 90%, 95%, 96%, 97%, 98%, 99%, or 100% identical to SEQ ID NO: 31. Also described is a nucleic acid molecule encoding a polypeptide comprising a chimeric antigen receptor (CAR), wherein the CAR comprises the amino acid sequence of SEQ ID NO: 30 or SEQ ID NO: 31 with no more than 5 (e.g., 1, 2, 3, 4 or 5) single amino acid changes. In certain embodiments the amino acid changes are entirely within the sequence

```
                                   (SEQ ID NO: 1)
QVQLVQSGAEVKKPGSSVKVSCKASGYTFTDYNMHWVRQAPGQGLEWIGYI

YPYNGGTGYNQKFKSKATITADESTNTAYMELSSLRSEDTAVYYCARGRPA

MDYWGQGTLVTVSSGGGGSGGGGSGGGGSDIQMTQSPSSLSASVGDRVTIT

CRASESVDNYGISFMNWFQQKPGKAPKLLIYAASNQGSGVPSRFSGSGSGT

DFTLTISSLQPDDFATYYCQQSKEVPWTFGQGTKVEIK
or the sequence (SEQ ID NO: 32)
QVQLVQSGAEVKKPGSSVKVSCKASGYTFTDYNMHWVRQAPGQGLEWIGYI

YPYNGGTGYNQKFKSKATITADESTNTAYMELSSLRSEDTAVYYCARGRPA

MDYWGQGTLVTVSS
or the sequence (SEQ ID NO: 33)
DIVMTQSPDSLAVSLGERATMSCKSSQSILYSSNQKNYLAWYQQKPGQSPK

LLIYWASTRESGVPDRFSGSGSGTDFTLTISSLQAEDVAVYYCHQYLSSYT

FGQGTKLEIK.
```

Also described is an expression vector comprising the nucleic acid molecule (e.g., a viral vector or a lentiviral vector). Also described is a population of human T cells or NK cells transduced by a vector or comprising the nucleic acid molecule described above. In various embodiments the cells comprise or consist of or consist essentially of: central memory T cells, naive memory T cells, pan T cells, NK cells, or PBMC substantially depleted for CD25+ cells and CD14+ cells.

Also described is method of treating a leukemia or a cancer in a patient comprising administering a population of autologous or allogeneic human T cells or NK transduced by a vector comprising the nucleic acid molecule described above or T cells or NK cells comprising a nucleic acid molecule described herein, wherein the leukemia comprises cells expressing CD33. In various embodiments: the chimeric antigen receptor is administered locally or systemically; the CD33-expressing cells are cancerous T cells or T-regulatory cells; the chimeric antigen receptor is administered by single or repeat dosing; the patient is administered a hypomethylating agent prior to or in conjunction the population of autologous or allogeneic human T cells; the hypomethylating agent is a DNA methyltransferase inhibitor; the hypomethylating agent is selected from 5-azacytidine and decitabine; the cancer is a hematologic cancer selected from the group acute myeloid leukemia (AML); myelodysplastic syndrome; myeloproliferative neoplasms; chronic myeloid leukemia (CML); and blastic plasmacytoid dendritic cell neoplasm.

Also described is method for reducing myeloid-derived suppressor cells (MDSC) in a patient suffering from cancer (e.g., a solid tumor) the method comprising administering immune cells comprising a nucleic acid molecule described herein to the patient. In some cases, the MDSC is lineage negative (LIN–), HLA-DR negative, and CD33 positive. In some case, a CD33 CAR-expressing cell described herein targets a MDS blast and a MDSC. In embodiments, a CD33 CAR-expressing cell described herein is used to treat multiple myeloma, chronic lymphocytic leukemia (CLL), or solid malignancies such as ovarian cancer, colon cancer, or breast cancer.

Also described is a method of preparing CD33 CAR T cells comprising: providing a population of autologous or allogeneic human T cells or NK and transducing the T cells or NK cells Described herein is a nucleic acid molecule comprising a nucleotide sequence encoding a chimeric antigen receptor (CAR), wherein the chimeric antigen receptor comprises: an scFv targeting CD33, a spacer, a transmembrane domain, a 41-BB co-stimulatory domain, and a CD3 signaling domain.

In various embodiments: the transmembrane domain is selected from: a CD4 transmembrane domain or variant thereof having 1-5 amino acid modifications, a CD8 transmembrane domain or variant thereof having 1-5 amino acid modifications, a CD28 transmembrane domain or a variant thereof having 1-5 amino acid modifications; the spacer comprises 20-150 amino acids and is located between the scFv and the transmembrane domain; the transmembrane domain is a CD4 transmembrane domain or variant thereof having 1-5 amino acid modifications; the transmembrane domain is a CD4 transmembrane domain; the chimeric antigen receptor comprises a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications; the spacer region comprises an amino acid sequence selected from the group consisting of SEQ ID NOs: 2-12 or a variant thereof having 1-5 amino acid modifications; the spacer comprises an IgG hinge region; the spacer comprises 10-50 amino acids; the 4-1BB costimulatory domain comprises the amino acid sequence of SEQ ID NO: 24 or a variant thereof having 1-5 amino acid modifications; the CD3 signaling domain comprises the amino acid sequence of SEQ ID NO:21; a linker of 3 to 15 amino acids is located between the 4-1BB costimulatory domain and the CD3 signaling domain or variant thereof; the CAR comprises the amino acid sequence of SEQ ID NO: 30 or 31 or a variant thereof having 1-5 amino acid modifications, e.g., 1-5 single amino acid substitutions; the scFv comprises the amino acid sequence of SEQ ID NO:1; the nucleic acid molecule of claim 1.

Also disclosed herein is: a viral vector comprising a nucleic acid molecule described herein; a population of human T cells (e.g., a population comprising central memory T cells) transduced by a vector comprising a nucleic acid molecule described herein.

Also described herein is a method of treating CD33 positive cancers (including, e.g., AML, R/R AML, acute lymphoblastic leukemia (ALL), myelodysplastic syndromes (MDS), myeloma, myeloproliferative neoplasms, other CD33$^+$ hematologic malignancies, and the like) in a patient comprising administering a population of autologous or allogeneic human T cells transduced by a vector comprising a nucleic acid molecule described herein, wherein the cancer (or disease or disorder) comprises cells expressing CD33. In various embodiments: the chimeric antigen receptor is administered locally or systemically; the CD33-expressing cells are cancerous T cells; and the chimeric antigen receptor is administered by single or repeat dosing.

In various embodiments: the chimeric antigen receptor comprises: a CD33 scFv (e.g., an scFv comprising the amino acid sequence QVQLVQSGAEVKKPGSSVKVSCK-ASGYTFTDYNMHWVRQAPGQGLEWIGYIYPYN GGTGYNQKFKSKATITADESTNTAYMELS SLRSED-TAVYYCARGRPAMDYWGQGT LVTVSSGGGGSGGGGSGGGGSDIQMTQSPSSL-SASVGDRVTITCRASESVDNYGISF MNWFQQKPGKAPKLLI-YAASNQGSGVPSRFSGSGSGTDFTLTISSLQPDDFA-TYYCQ QSKEVPWTFGQGTKVEIK (SEQ ID NO:1) with up to 10 single amino acid substitutions.

Also described are T cells harboring a vector expressing the CD33 CAR. In various embodiments: at least 20%, 30%, or 40% of the transduced human T cells are central memory T cells; at least 30% of the transduced human T cells are CD4+ and CD62L+ or CD8+ and CD62L+. In various embodiments: the population of human T cells comprise a vector expressing a chimeric antigen receptor comprising an amino acid sequence selected from SEQ ID NOs: 30 or 31 or a variant thereof having 1-5 amino acid modifications (e.g., 1 or 2) amino acid modifications (e.g., substitutions); the population of human T cells comprises central memory T cells (T$_{CM}$ cells) e.g., at least 20%, 30%, 40%, 50% 60%, 70%, 80% of the cells are T cm cells, or the population of T cells comprises a combination of central memory T cells, naïve T cells and stem central memory cells (T$_{CM/SCM/N}$ cells) e.g., at least 20%, 30%, 40%, 50% 60%, 70%, 80% of the cells are T$_{CM/SCM/N}$ cells. In some embodiments, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells). In some embodiments, the population of human T cells are autologous to the patient. In some embodiments, the population of human T cells are allogenic to the patient.

CD33 Targeted CAR

The CD33 targeted CAR described herein include a CD33 targeting scFv. In some embodiments, an scFv comprising the amino acid sequence:

```
                                       (SEQ ID NO: 1)
QVQLVQSGAEVKKPGSSVKVSCKASGYTFTDYNMHWVRQAPGQGLEWIGYI

YPYNGGTGYNQKFKSKATITADESTNTAYMELSSLRSEDTAVYYCARGRPA

MDYWGQGTLVTVSSGGGGSGGGGSGGGGSDIQMTQSPSSLSASVGDRVTIT

CRASESVDNYGISFMNWFQQKPGKAPKLLIYAASNQGSGVPSRFSGSGSGT

DFTLTISSLQPDDFATYYCQQSKEVPWTFGQGTKVEIK
or comprising the sequence
                                      (SEQ ID NO: 32)
QVQLVQSGAEVKKPGSSVKVSCKASGYTFTDYNMHWVRQAPGQGLEWIGYI

YPYNGGTGYNQKFKSKATITADESTNTAYMELSSLRSEDTAVYYCARGRPA

MDYWGQGTLVTVSS
and the sequence
                                      (SEQ ID NO: 33)
DIVMTQSPDSLAVSLGERATMSCKSSQSILYSSNQKNYLAWYQQKPGQSPK

LLWWASTRESGVPDRFSGSGSGTDFTLTISSLQAEDVAVYYCHQYLSSYTF

GQGTKLEIK
joined by a flexible linker.
```

A useful CD33 CAR can consist of or comprises the amino acid sequence of SEQ ID NO: 30 or 31 (mature CAR lacking a signal sequence) or the CD33 CAR can consist of or comprise the amino acid sequence of SEQ ID NO: 30 or 31 preceded by a GMCSFRa signal sequence (SEQ ID NO: 34) (immature CAR having a GMCSFRa signal sequence; (MLLLVTSLLLCELPHPAFLLIP; SEQ ID NO:34). =The CAR can be expressed with additional sequences that are useful for monitoring expression, for example, a T2A skip sequence and a truncated EGFRt. The CAR can be expressed with additional sequences that are useful for monitoring expression, for example, a T2A skip sequence and a truncated CD19t. Thus, the CAR can comprise or consist of the amino acid sequence of SEQ ID Nos: 30, or a hinge portion of a human Fc region or a CH3 domain or variants thereof. Table 1 below provides various spacers that can be used in the CARS described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHLCPSPLFPGPSKP (SEQ ID NO: 6) |
| CD8 hinge-48aa | 48 aa | AKPTTTPAPRPPTPAPTIASQPLSLRPEACRPAAGGAVHTRGLDFACD (SEQ ID NO: 7) |
| CD8 hinge-45aa | 45aa | TTTPAPRPPTPAPTIASQPLSLRPEACRPAAGGAVHTRGLDFACD (SEQ ID NO: 8) |
| IgG4(HL-CH3) (includes S228P in hinge) | 129 aa | ESKYGPPCPPCPGGGSSGGGSGGQPREPQVYTLPPSQEEMTKNQVSLTCL VKGFYPSDIAVEWESNGQPENNYKTTPPVLDSDGSFFLYSRLTVDKSRWQE GNVFSCSVMHEALHNHYTQKSLSLSLGK (SEQ ID NO: 9) |
| IgG4(L235E, N297Q) | 229 aa | ESKYGPPCPSCPAPEFEGGPSVFLFPPKPKDTLMISRTPEVTCVVVDVSQED PEVQFNWYVDGVEVHQAKTKPREEQFQSTYRVVSVLTVLHQDWLNGKEY KCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGN VFSCSVMHEALHNHYTQKSLSLSLGK (SEQ ID NO: 10) |
| IgG4(S228P, L235E, N297Q) | 229 aa | ESKYGPPCPPCPAPEFEGGPSVFLFPPKPKDTLMISRTPEVTCVVVDVSQED PEVQFNWYVDGVEVHQAKTKPREEQFQSTYRVVSVLTVLHQDWLNGKEY KCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGN VFSCSVMHEALHNHYTQKSLSLSLGK (SEQ ID NO: 11) |
| IgG4(CH3) | 107 aa | GQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSL SLSLGK (SEQ ID NO: 12) |

31 or can comprise or consist of an amino acid sequence that is at least 95%, 96%, 97%, 98% or 99% identical to SEQ ID Nos: 30, or 31. The CAR can comprise or consist of the amino acid sequence of any of SEQ ID Nos: 30, or 31 with up to 1, 2, 3, 4 or 5 amino acid changes (preferably conservative amino acid changes). The CAR can comprise an scFv targeted to CD33, e.g., an scFv comprising SEQ ID NO: 1 with up to 1, 2, 3, 4 or 5 amino acid changes (preferably conservative amino acid changes or an scFv comprising SEQ ID NO:32 with up to 1, 2, 3, 4 or 5 amino acid changes (preferably conservative amino acid changes) and SEQ ID NO:33 with up to 1, 2, 3, 4 or 5 amino acid changes (preferably conservative amino acid changes) joined by a flexible linker.

In some embodiments, the nucleic acid encoding amino acid sequences SEQ ID NOs:1-34 are codon optimized. In some embodiments, the nucleic acid encoding amino acid sequences SEQ ID NOs:1-34 are not codon optimized.

Spacer Region

The CAR described herein can include a spacer located between the CD33 targeting domain (i.e., a CD33 targeted ScFv or variant thereof) and the transmembrane domain. A variety of different spacers can be used. Some of them include at least portion of a human Fc region, for example Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise a IgG4 hinge region having the sequence ESKYGPPCPSCP (SEQ ID NO:4) or ESKYGPPCPPCP (SEQ ID NO:3). The hinge/linger region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO:12). Thus, the entire linker/spacer region can comprise the sequence: ESKYGPPCPPCPGGGS SGGGSGGQPREPQVYTLPP SQEEMTKNQVSLTCLVKGFYPS DIAVEWESNGQPEN-NYKTTPPVLDSDGSFFLY-SRLTVDKSRWQEGNVFSCSVMHEA LHN-HYTQKSLSLSLGK (SEQ ID NO:11). In some cases, the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Domain

A variety of transmembrane domains can be used in the. Table 2 includes examples of suitable transmembrane domains. Where a spacer region is present, the transmembrane domain (TM) is located carboxy terminal to the spacer region.

TABLE 2

| Examples of Transmembrane Domains | | | |
|---|---|---|---|
| Name | Accession | Length | Sequence |
| CD3z | J04132.1 | 21 aa | LCYLLDGILFIYGVILTALFL (SEQ ID NO: 13) |
| CD28 | NM_006139 | 27aa | FWVLVVVGGVLACYSLLVTVAFIIF WV (SEQ ID NO: 14) |
| CD28(M) | NM_006139 | 28aa | MFWVLVVVGGVLACYSLLVTVAFII FWV (SEQ ID NO: 15) |
| CD4 | M35160 | 22aa | MALIVLGGVAGLLLFIGLGIFF (SEQ ID NO: 16) |
| CD8tm | NM_001768 | 21aa | IYIWAPLAGTCGVLLLSLVIT (SEQ ID NO: 17) |
| CD8tm2 | NM_001768 | 23aa | IYIWAPLAGTCGVLLLSLVITLY (SEQ ID NO: 18) |
| CD8tm3 | NM_001768 | 24aa | IYIWAPLAGTCGVLLLSLVITLYC (SEQ ID NO: 19) |
| 41BB | NM_001561 | 27aa | IISFFLALTSTALLFLLFFLTLRF SVV (SEQ ID NO: 20) |

Costimulatory Domain

The costimulatory domain can be any domain that is suitable for use with a CD3 signaling domain. In some cases the co-signaling domain is a 4-1BB co-signaling domain that includes a sequence that is at least 90%, at least 95%, at least 98% identical to or identical to: KRGRKKLLY-IFKQPFMRPVQTTQEEDGCSCRFPEEEEGGCEL (SEQ ID NO:24). In some cases, the 4-1BB co-signaling domain has 1, 2, 3, 4 of 5 amino acid changes (preferably conservative) compared to SEQ ID NO:24.

The costimulatory domain(s) are located between the transmembrane domain and the CD3 signaling domain. Table 3 includes examples of suitable costimulatory domains together with the sequence of the CD3 signaling domain.

TABLE 3

| CD3ζ Domain and Examples of Costimulatory Domains | | | |
|---|---|---|---|
| Name | Accession | Length | Sequence |
| CD3ζ | J04132.1 | 113 aa | RVKFSRSADAPAYQQGQNQLYNEL NLGRREEYDVLDKRRGRDPEMGGK PRRKNPQEGLYNELQKDKMAEAYS |

TABLE 3-continued

| CD3ζ Domain and Examples of Costimulatory Domains | | | |
|---|---|---|---|
| Name | Accession | Length | Sequence |
| | | | EIGMKGERRRGKGHDGLYQGLSTA TKDTYDALHMQALPPR (SEQ ID NO: 21) |
| CD28 | NM_006139 | 42aa | RSKRSRLLHSDYMNMTPRRPGPTR KHYQPYAPPRDFAAYRS (SEQ ID NO: 22) |
| CD28gg* | NM_006139 | 42aa | RSKRSRGGHSDYMNMTPRRPGPTR KHYQPYAPPRDFAAYRS (SEQ ID NO: 23) |
| 41BB | NM_001561 | 42 aa | KRGRKKLLYIFKQPFMRPVQTTQE EDGCSCRFPEEEEGGCEL (SEQ ID NO: 24) |
| OX40 | | 42 aa | ALYLLRRDQRLPPDAHKPPGGGSF RTPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3 signaling domain and a short linker consisting of 2-10, e.g., 3 amino acids (e.g., GGG) is can be positioned between the costimulatory domain and the CD3 signaling domain.

CD3ζ Signaling Domain

The CD3ζ Signaling domain can be any domain that is suitable for use with a CD3ζ signaling domain. In some cases, the CD3 signaling domain includes a sequence that is at least 90%, at least 95%, at least 98% identical to or identical to: RVKFSRSADAPAYQQGQNQLYNELNLGR-REEYDVLDKRRGRDPEMGGKPRRKNPQ EGLY-NELQKDKMAEAYSEIGMKGERRRGKGHDGLYQGL-STATKDTYDALHMQAL PPR (SEQ ID NO:21). In some cases, the CD3ζ signaling has 1, 2, 3, 4 of 5 amino acid changes (preferably conservative) compared to SEQ ID NO:21.

Truncated EGFR and Truncated CD19

The CD3ζ signaling domain can be followed by a ribosomal skip sequence (e.g., LEGGGEGRGSLLTCGD-VEENPGR; SEQ ID NO:27) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDL-HILPVA FRGDSFTHTPPLDPQELDILKTVKEITGFLL-IQAWPENRTDLHAFENLEIIRGRTKQHG QFSLAVVSL- NITSLGLRSLKEISDGDVIISGNKNLCYA-
NTINWKKLFGTSGQKTKIISN RGENSCK-
ATGQVCHALCSPEGCWGPEPRDCVSCRNVSR-
GRECVDKCNLLEGEPREF
VENSECIQCHPECLPQAMNITCTGRGPDNCI-
QCAHYIDGPHCVKTCPAGVMGENNTL VWKY-
ADAGHVCHLCHPNCTYGCTGPGLEGCPTNGPKIPSI-
ATGMVGALLLLLVVAL GIGLFM (SEQ ID NO:28). In
some cases, the truncated EGFR has 1, 2, 3, 4 of 5 amino
acid changes (preferably conservative) compared to SEQ ID
NO:28.

Alternatively the CD3 signaling domain can be followed
by a ribosomal skip sequence (e.g.,
LEGGGEGRGSLLTCGDVEENPGPR; SEQ ID NO:27)
and a truncated CD19R having a sequence that is at least
90%, at least 95%, at least 98% identical to or identical to:

```
                                        (SEQ ID NO: 26)
MPPPRLLFFLLFLTPMEVRPEEPLVVKVEEGDNAVLQCLKGTSDGPTQQLT

WSRESPLKPFLKLSLGLPGLGIHMRPLAIWLFIFNVSQQMGGFYLCQPGPP

SEKAWQPGWTVNVEGSGELFRWNVSDLGGLGCGLKNRSSEGPSSPSGKLMS

PKLYVWAKDRPEIWEGEPPCVPPRDSLNQSLSQDLTMAPGSTLWLSCGVPP

DSVSRGPLSWTHVHPKGPKSLLSLELKDDRPARDMWVMETGLLLPRATAQD

AGKYYCHRGNLTMSFHLEITARPVLWHWLLRTGGWKVSAVTLAYLIFCLCS

LVGILHLQRALVLRRKR
```

An amino acid modification refers to an amino acid
substitution, insertion, and/or deletion in a protein or peptide
sequence. An "amino acid substitution" or "substitution"
refers to replacement of an amino acid at a particular
position in a parent peptide or protein sequence with another
amino acid. A substitution can be made to change an amino
acid in the resulting protein in a non-conservative manner
(i.e., by changing the codon from an amino acid belonging
to a grouping of amino acids having a particular size or
characteristic to an amino acid belonging to another group-
ing) or in a conservative manner (i.e., by changing the codon
from an amino acid belonging to a grouping of amino acids
having a particular size or characteristic to an amino acid
belonging to the same grouping). Such a conservative
change generally leads to less change in the structure and
function of the resulting protein. The following are examples
of various groupings of amino acids: 1) Amino acids with
nonpolar R groups: Alanine, Valine, Leucine, Isoleucine,
Proline, Phenylalanine, Tryptophan, Methionine; 2) Amino
acids with uncharged polar R groups: Glycine, Serine,
Threonine, Cysteine, Tyrosine, Asparagine, Glutamine; 3)
Amino acids with charged polar R groups (negatively
charged at pH 6.0): Aspartic acid, Glutamic acid; 4) Basic
amino acids (positively charged at pH 6.0): Lysine, Argi-
nine, Histidine (at pH 6.0). Another grouping may be those
amino acids with phenyl groups: Phenylalanine, Trypto-
phan, and Tyrosine.

In some cases, the CD33 CAR can be produced using a
vector in which the CAR open reading frame is followed by
a T2A ribosome skip sequence and a truncated EGFR
(EGFRt), which lacks the cytoplasmic signaling tail. In this
arrangement, co-expression of EGFRt provides an inert,
non-immunogenic surface marker that allows for accurate
measurement of gene modified cells, and enables positive
selection of gene-modified cells, as well as efficient cell
tracking of the therapeutic T cells in vivo following adoptive
transfer. Efficiently controlling proliferation to avoid cytokine storm and off-target toxicity is an important hurdle for
the success of T cell immunotherapy. The EGFRt incorpo-
rated in the CD33 CAR lentiviral vector can act as suicide
gene to ablate the CAR+ T cells in cases of treatment-related
toxicity.

The CAR described herein can be produced by any means
known in the art, though preferably it is produced using
recombinant DNA techniques. Nucleic acids encoding the
several regions of the chimeric receptor can be prepared and
assembled into a complete coding sequence by standard
techniques of molecular cloning known in the art (genomic
library screening, overlapping PCR, primer-assisted liga-
tion, site-directed mutagenesis, etc.) as is convenient. The
resulting coding region is preferably inserted into an expres-
sion vector and used to transform a suitable expression host
cell line, preferably a T lymphocyte, and most preferably an
autologous T lymphocyte.

Various T cell subsets isolated from the patient can be
transduced with a vector for CAR expression. Central
memory T cells are one useful T cell subset. Central memory
T cell can be isolated from peripheral blood mononuclear
cells (PBMC) by selecting for CD45RO+/CD62L+ cells,
using, for example, the CliniMACS® device to immuno-
magnetically select cells expressing the desired receptors.
The cells enriched for central memory T cells can be
activated with anti-CD3/CD28, transduced with, for
example, a lentiviral vector that directs the expression of an
CD33 CAR as well as a non-immunogenic surface marker
for in vivo detection, ablation, and potential ex vivo selec-
tion. The activated/genetically modified CD33 central
memory T cells can be expanded in vitro with IL-2/IL-15
and then cryopreserved. Additional methods of preparing
CART cells can be found in PCT/US2016/043392.

In another aspect, the CD33 CAR expressing cell is an
immune effector cell such as T cell or an NK cell that harbor
an exogenous RNA molecule, e.g., an in vitro transcribed
RNA or synthetic RNA comprising nucleic molecule acid
encoding a CAR molecule described herein.

Unless otherwise defined, all technical and scientific
terms used herein have the same meaning as commonly
understood by one of ordinary skill in the art to which this
invention belongs. Methods and materials are described
herein for use in the present invention; other, suitable
methods and materials known in the art can also be used.
The materials, methods, and examples are illustrative only
and not intended to be limiting. All publications, patent
applications, patents, sequences, database entries, and other
references mentioned herein are incorporated by reference in
their entirety for any and all purposes. In case of conflict, the
present specification, including definitions, will control.

Other features and advantages of the invention will be
apparent from the following detailed description and figures,
and from the claims.

DESCRIPTION OF DRAWINGS

FIG. 2A) and CD33 CAR T
cells (FIG. 2B) were elevated by flow cytometry for EGFR
expression to detect expression of CARS. Both mock and
CD33 CAR T cells exhibited robust expansion during ex
vivo culture (FIG. 2C).

FIG. 4A shows results from degranulation assay using an E:T ratio of 2:1 of mock or CD33 CART cells against AML cells. FIG. 4B shows results from intracellular IFN-γ staining assay using an E:T ratio of 1:1 of mock or CD33 CAR T cells against AML cells. FIG. 4C shows results from rechallenge assay using E:T ratios of 1:5, 1:10, and 1:20 of mock or CD33 CART cells against AML cells. RAJI cell line was used as a negative control.

FIG. 6A shows $3 \times 10^6$ CD33 CART cells, compared with $3 \times 10^6$ mock T cells or untreated groups, significantly reduced leukemic burden in vivo. FIG. 6B shows $3 \times 10^6$ CD33 CART cells, compared with $3 \times 10^6$ mock T cells or untreated groups, significantly prolonged overall survival in vivo.

FIG. 11A shows 0.5 mg/kg/d×5 d decitabine, followed by $1 \times 10^6$ CD33 CART cells, significantly decreased leukemic burden in vivo. FIG. 11B shows combinational treatment of 0.5 mg/kg/d×5 d decitabine and $1 \times 10^6$ CD33 CART cells significantly prolonged overall survival in vivo.

FIGS. 14A-14B show the annotated amino acid sequences of CD33 CD8 CAR (A; SEQ ID NO:30) and CD33 EQ CAR (B; SEQ ID NO:31). The alternating underlining indicates the various components.

FIGS. 15A-15F show the annotated nucleic acid and corresponding amino acid sequences of (A-C) CD33 CD8 CAR preceded by a GMCSR signal sequence and followed by a T2A skip sequence and EGFRt (SEQ ID NO: 35 (nucleic acid) and SEQ ID NO: 36 (amino acid)); and (D-F)

CD33 EQ CAR preceded by a GMCSR signal sequence and followed by a T2A skip sequence and EGFRt (SEQ ID NO: 35 (nucleic acid) and SEQ ID NO: 36 (amino acid)). The codon optimized portions of each nucleic acid sequence are in bold.

DETAILED DESCRIPTION

In this disclosure the generation and anti-tumor efficacy of CAR with a humanized anti-human CD33 scFv antigen-binding domain and, in some embodiments, a 4-1BB intracellular co-stimulatory signaling domain are described. The CD33 CAR T cells exhibited potent antigen-dependent cytotoxicity against CD33-expressing human cancer lines. Intraperitoneal or intravenous in vivo delivery of CD33 CART cells in human leukemia/lymphoma murine tumor models conferred elimination of antigen-positive disease and extension of overall survival.

EXAMPLES

The invention is further described in the following examples, which do not limit the scope of the invention described in the claims.

Example 1: Construction of CD33 CAR T Cells Containing Differing Linkers

The studies described below show that CD33 CAR can be stably expressed on primary T cells.

Figure 1:
FIG. 1 shows a schematic depicting a representative
CD33 CAR construct.

Multiple CD33-targeting CAR constructs were designed. All of the constructs expressed the same codon optimized, humanized CD33 single chain variable fragment. In some embodiments, the CAR constructs also included a CD4 transmembrane domain (TM), a 41BB costimulatory domain, a CD3 zeta domain. In some embodiments, the CAR constructs also included a CD8 transmembrane domain (TM), a 41BB costimulatory domain, a CD3 zeta domain. A representative schematic of a CD33 CAR is shown in FIG. 1. The CARs were co-expressed with truncated EGFR, which served as a marker for the successful transduction of the cells with the CAR construct. In some embodiments, the CD33 CAR constructs differ in their linker and transmembrane domains. Without being bound by theory, differing lengths in the extracellular portion of the construct may provide differences in the CARS ability to bind the antigen and transmit activation signals after antigen binding. These differences could also result differential killing of CD33 expressing tumor cells.

FIG. 14A depicts the amino acid sequence of a CD33 CAR comprising a CD33-targeted scFv, a CD8 hinge (spacer), a CD8 transmembrane domain, a 41-BB co-stimulatory domain joined by a GGG linker to a CD3 zeta stimulatory domain (SEQ ID NO: 30). FIG. 14B depicts the amino acid sequence of a CD33 CAR comprising a CD33-targeted scFv, an IgG4 spacer (IgG4 (S228P, L235E, N297Q)), a CD4 transmembrane domain, a 41-BB co-stimulatory domain joined by a GGG linker to a CD3 zeta stimulatory domain (SEQ ID NO: 31).

Figure 2A:
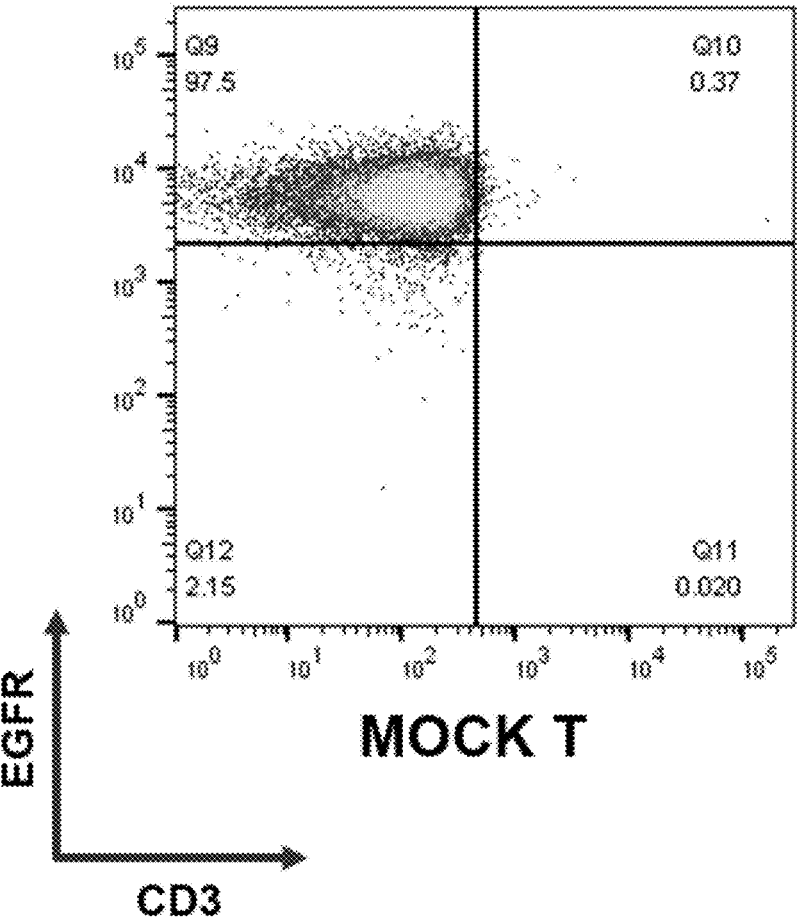
FIGS. 2A-2C show results from experiments with CD33
(CD8) CAR T cells where EGFRt is used as a tracking
marker and its expression was stable through 13 days culture
duration. Mock (untransduced.
Figure 2B:
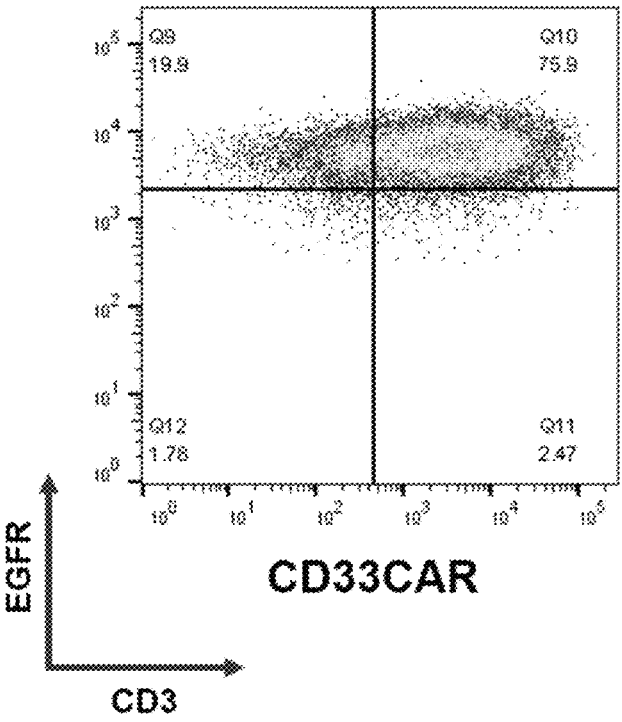
Figure 2C:
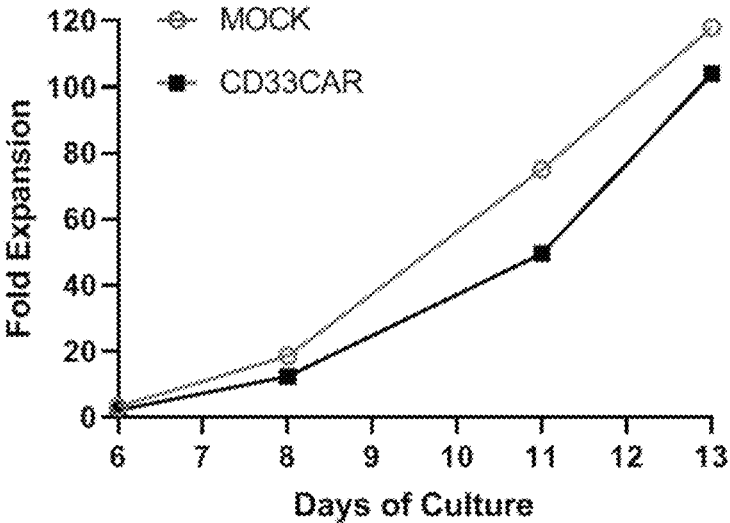

CD33 CAR lentivirus was used to transduce human healthy donor-derived peripheral blood mononuclear cells depleted of CD14+ and CD25+ cells (dPBMC), T(n/mem) cells, Pan T cells, as previously described (Priceman S J, Gerdts E A, Tilakawardane D, Kennewick K T, Murad J P, Park A K, Jeang B, Yamaguchi Y, Yang X, Urak R, Weng L, Chang W C, Wright S, Pal S, Reiter R E, Wu A M, Brown C E, Forman S J. Co-stimulatory signaling determines tumor antigen sensitivity and persistence of CAR T cells targeting PSCA+metastatic prostate cancer. Oncoimmunology. 2018; 7(2):e1380764), as well as other cells types such as enriched T-cells (EasySep Human T cell isolation Kit. StemCell Technologies). Using EGFRt as a tracking marker, flow cytometry was used to show CAR expression as described above. A representative CD33 CAR construct was stably expressed in T cells (FIGS. 2A-2C). Seven days after cells were transduced, cells were stained with anti-EGFR to mark successful incorporation of the CD33 CAR construct. The CD33 (CD8) CAR was stably expressed at 15 days post-transduction (FIG. 2C).

Example 2: CD33 Expression in AML Cell Lines

The studies described below examined CD33 expression on various AML cell lines.

Figure 3:
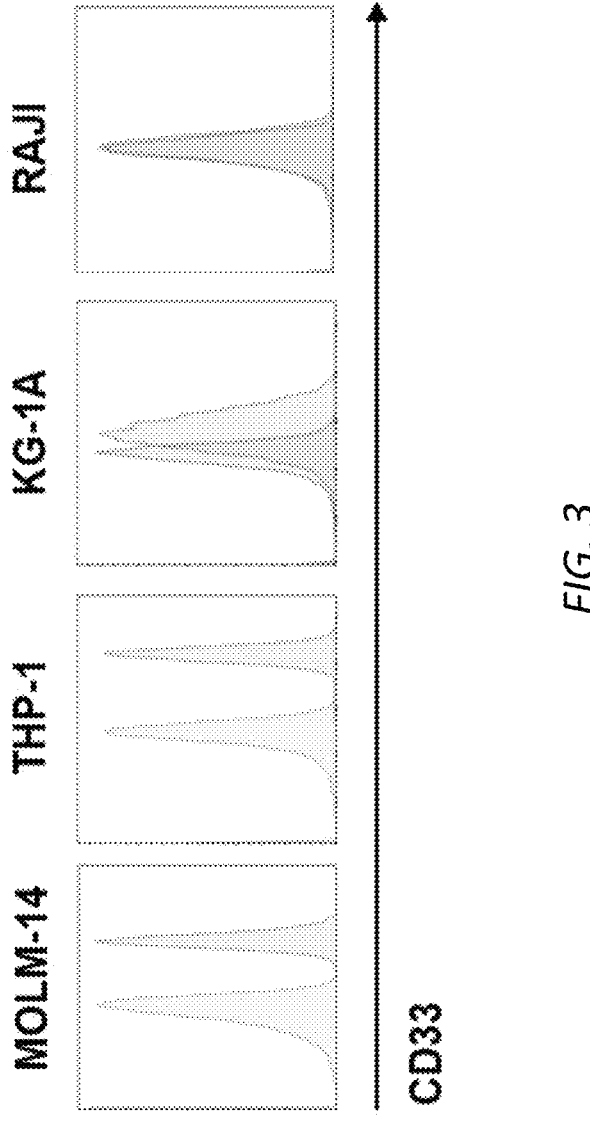
FIG. 3 shows CD33 expression on human AML cell lines. Human Burkitt's lymphoma cell line RAJI was used as a negative control.

As shown in FIG. 3, CD33 expression was highest in MOLM-14 and THP-1 cell lines. The KG-1A cell line exhibited intermediate CD33 expression. CD33 expression was lowest in the Raji cell line.

Example 3: CD33 CAR T Cells Exhibit Potent and Specific Cell Killing and Effector Function In Vitro To determine if CD33 CAR T cells demonstrate selective effector functions and killing activities against CD33-positive cancer cells, the CD33 CAR T cells were grown in presence of either CD33-positive or CD33-negative cancer cells. Then CD107a degranulation levels, intracellular IFN-γ staining, and the percentage of cancerous cells killed were quantified. The schematic of the assays used is shown in FIG. 4.

Figure 4A:
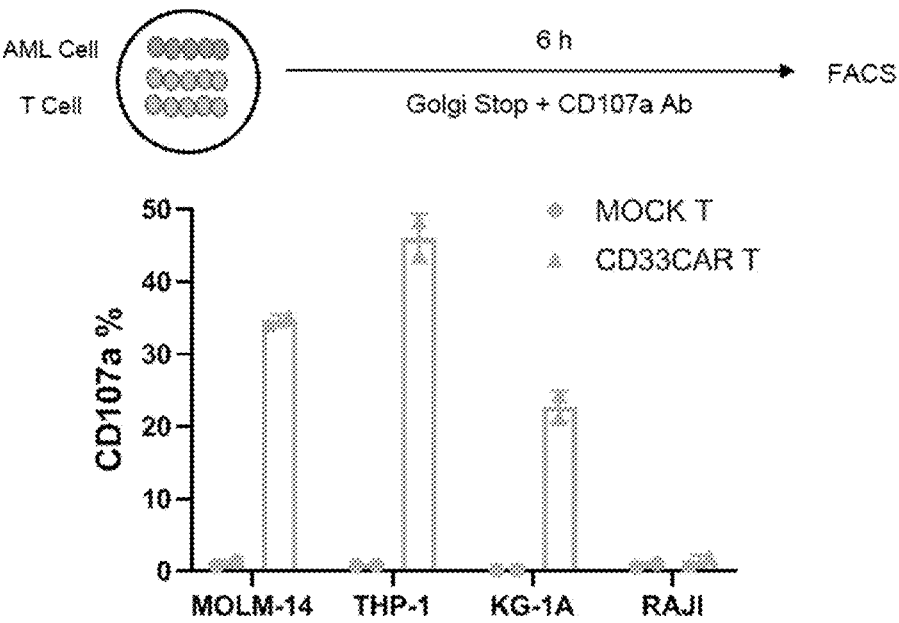
FIGS. 4A-4C shows effector functions and killing activities of CD33 (CD8) CAR T cells against CD33-expressing AML cell lines.
Figure 4B:
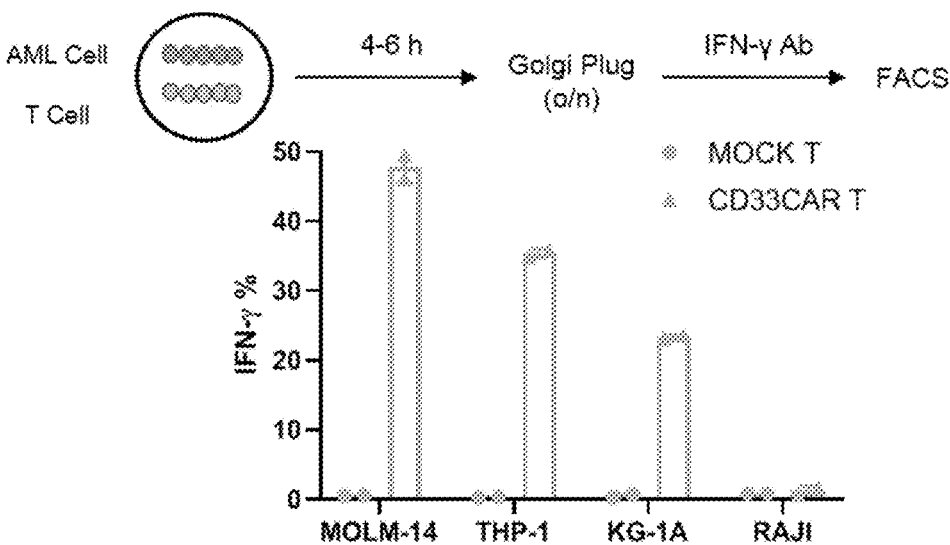

For CD107a degranulation assay, mock or CD33 CART cells were co-cultured with target cells at an E:T ratio of 2:1 in complete X-VIVO medium supplemented with Golgi Stop and CD107a antibody for 6 hours, followed by flow cytometry. The CD33-positive AML cell lines were MOLM-14, THP-1, and KG-1A. The CD33-negative cell line used was RAJI (FIG. 4A). For intracellular IFN-γ staining assay, mock or CD33 CAR T cells were co-cultured with target cells at an E:T ratio of 1:1 in complete X-VIVO medium for 4-6 hours. The cultures were then supplemented with Golgi Plug for overnight incubation. Next, the cells were fixed, permeabilized, stained with IFN-γ antibody, and subjected to flow cytometry (FIG. 4B). For rechallenge assay, mock or CD33 CAR T cells were co-cultured with target cells at E:T ratios of 1:5, 1:10, and 1:20 for 48 hours. After the 48 hours, we added additional tumor cells to the co-culture wells to an E:T of 1:5, 1:10, or 1:20, repeated the 48 hour incubation, and added additional tumor cells to the co-culture wells to an E:T of 1:5, 1:10, or 1:20. After an additional 48 hours, flow cytometry was used to determine the % specific lysis of the tumor cells (FIG. 4C).

Figure 4C:
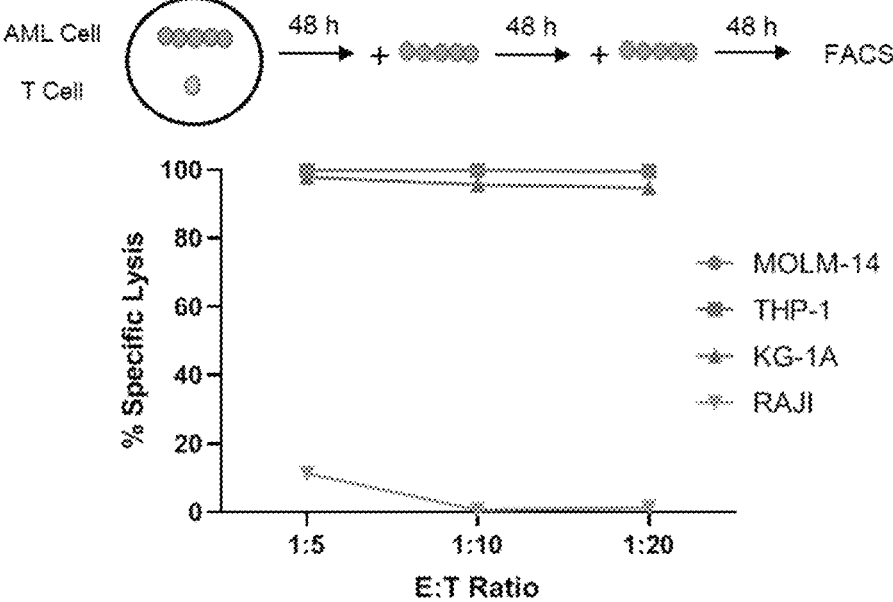

The CD33 (CD8) CART cells showed potent and specific CD107a degranulation levels, intracellular IFN-γ staining, and killing activities against CD33-positive AML cell lines, in comparison with CD33-negative RAJI cell line (FIGS. 4A-4C).

Example 5: Validation that CD33 CAR T Cells Delivered In Vivo in a Mouse Model Exhibit Potent Anti-Tumor Activity and Confer Extended Lifespan to the Mice To evaluate in vivo efficacy of CD33 CART cells to selectively target CD33-positive cells in the MOLM-14 model, CD33 CART cells were delivered and tumor size and survival was evaluated over time.

Figure 5:
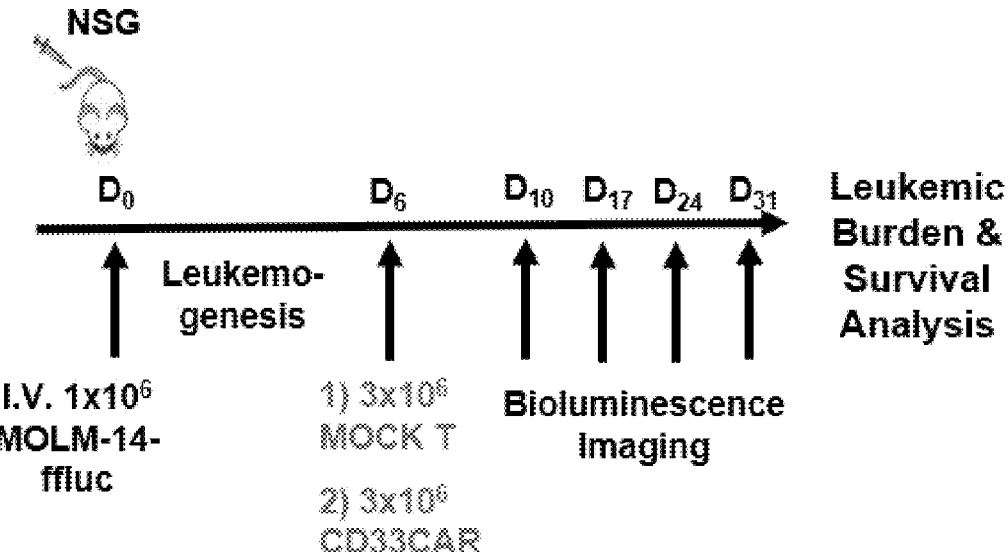
FIG. 5 shows a representative in vivo study using a NOD-SCID-IL2Rg$^{null}$ (NSG) xenograft model with MOLM-14-ffluc cell line, an AML cell line with high CD33 expression levels.
Figure 6A:
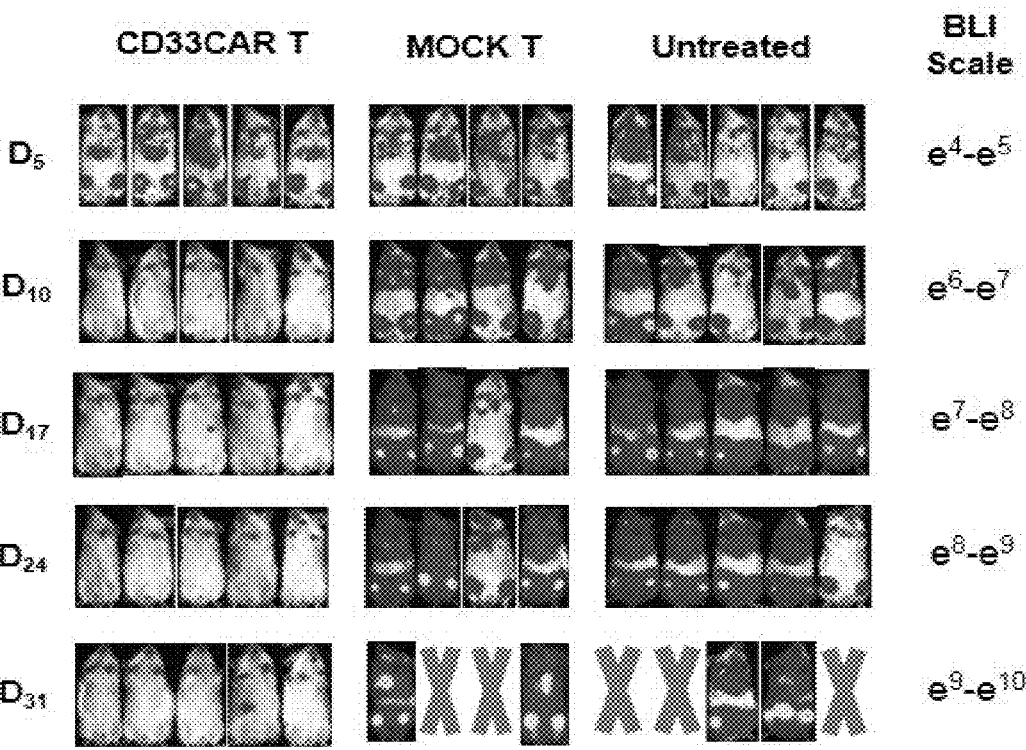
FIGS. 6A-6B show the ability of CD33 (CD8) CAR T cells to kill CD33-expressing tumor lines in vivo.
Figure 6B:
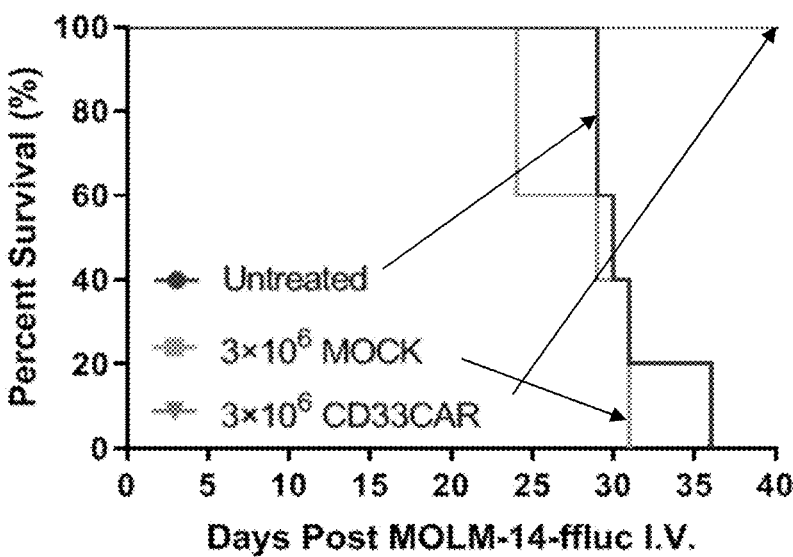

MOLM-14 cells were lentivirally transduced to express firefly luciferase (ffluc) to allow for tracking of tumor growth via non-invasive optical imaging. At 6 days post tumor intravenous injection, mice were treated with Mock or CD33 CAR T cells ($3 \times 10^6$) by systemic intravenous (i.v.) delivery (FIG. 5). Rapid anti-tumor effects were observed in mice treated with CD33 (CD8) CAR T cells via intravenous delivery, reaching a maximal anti-tumor response 1-2 weeks following treatment (FIG. 6A). Anti-tumor responses in mice were durable for 3-4 weeks. Delivery of CD33 (CD8) CART cells significantly extended survival of mice (FIG. 6B).

Figure 7:
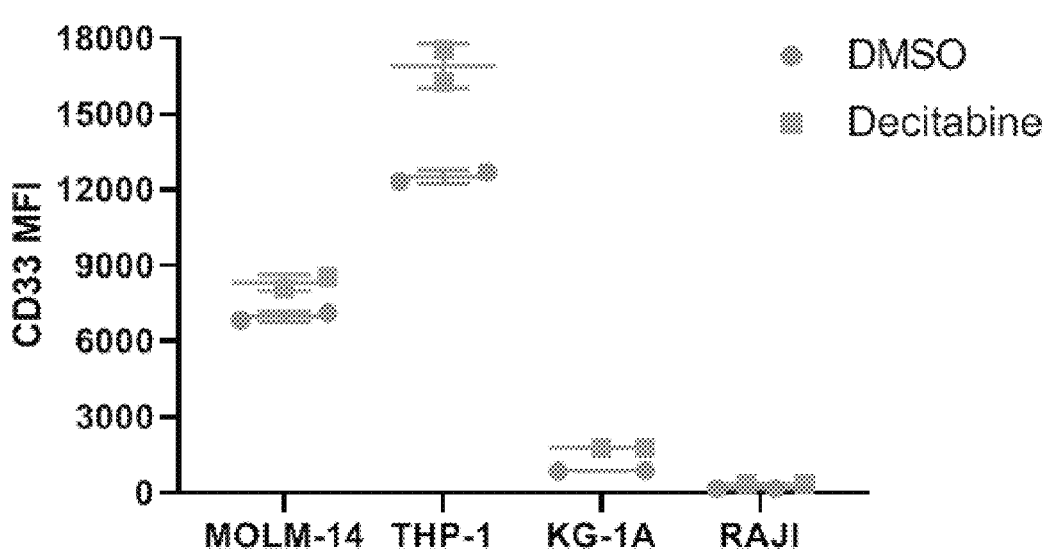
FIG. 7 shows CD33 expression on AML cell lines in the presence of 100 nM decitabine or DMSO for 2 consecutive days. RAJI cell line was used as a negative control.

Example 6: Decitabine Potentiates CD33 CAR T Cell-Mediated AML Killing In Vitro Decitabine is a commonly used hypomethylating agent (HMA) for AML treatment. We first treated AML cell lines with 100 nM decitabine or DMSO for 2 consecutive days. RAJI cell line was used as a negative control. We observed decitabine treatment led to upregulation of CD33 expression on AML cells (FIG. 7).

Figure 8:
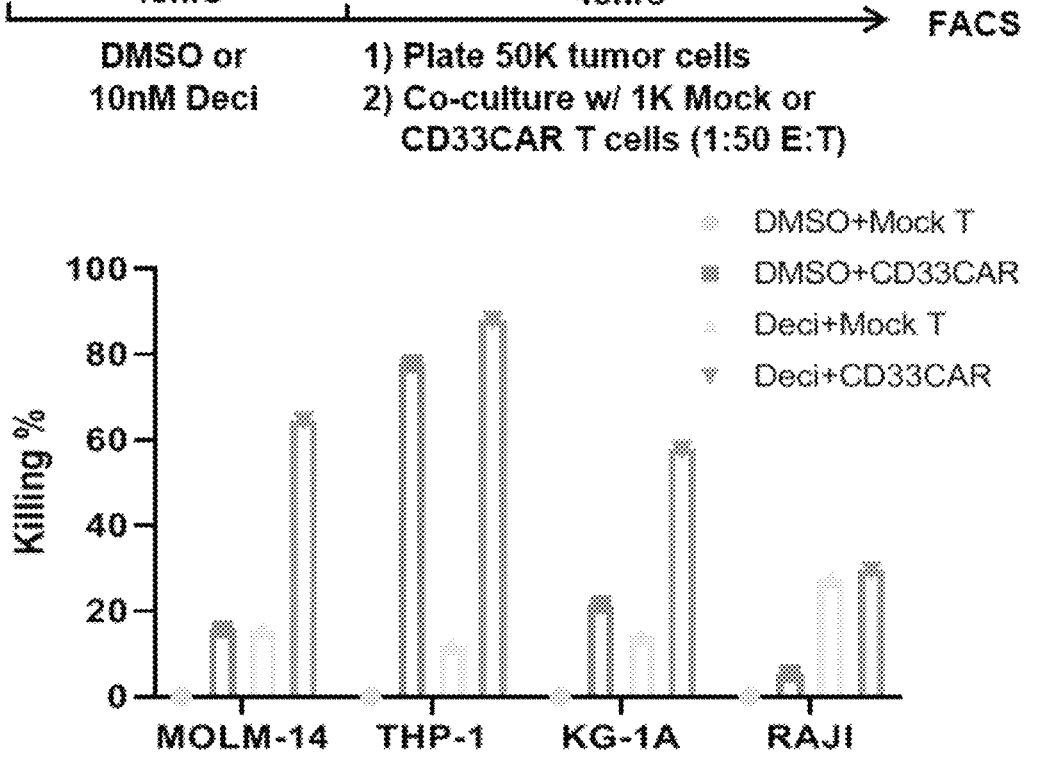
FIG. 8 shows a schematic depicting the killing activities of decitabine in combination with CD33 (CD8) CART cells in vitro. AML cell lines were treated with 10 nM decitabine or DMSO for 2 consecutive days, followed by CD33 CAR or mock T cells in an E:T ratio of 1:50. Another 48 hours later, the killing activities in each group were determined using flow cytometry. RAJI cell line was used as a negative control.

We hypothesized decitabine can potentiate CD33 CAR T cell-mediated AML killing. For in vitro combinational studies, AML cell lines were treated with 10 nM decitabine or DMSO for 2 consecutive days, followed by CD33 (CD8) CAR or mock T cells at an E:T ratio of 1:50. Another 48 hours later, the killing percentages (%) in each group were quantified using flow cytometry. In vitro experiments using AML cells as targets, the robust killing was seen in the group treated with decitabine followed by CD33 CAR T cells (FIG. 8).

Figure 9A:
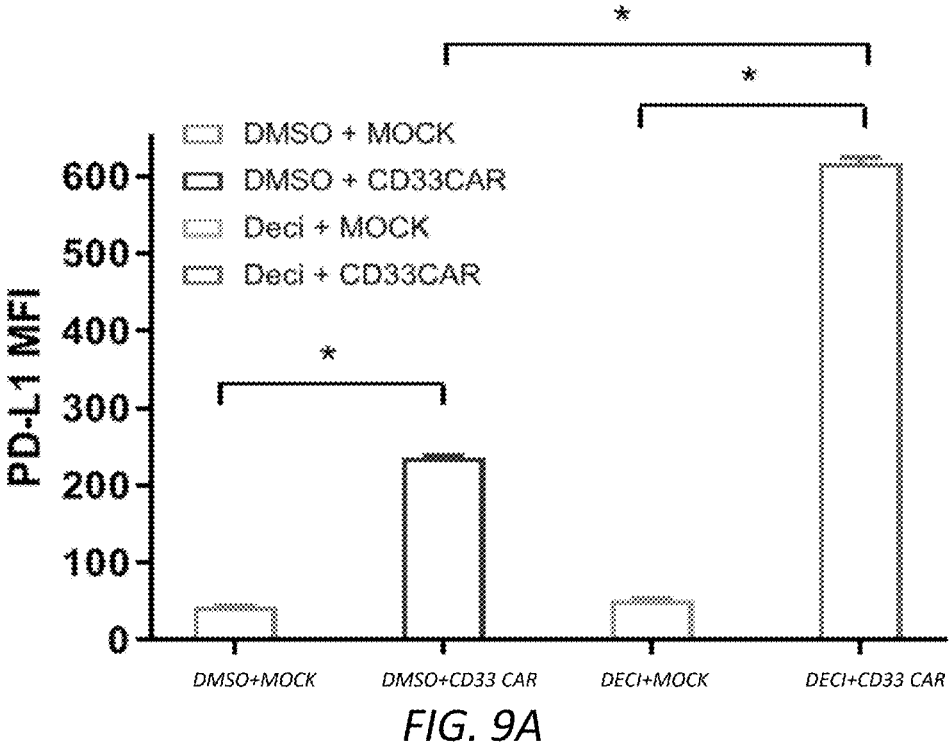
FIGS. 9A-9B show mean fluorescence intensities (MFI) of programmed death-ligand 1 (PD-L1) and c-type lectin-like molecule-1 (CLL-1) expression on residual AML cells, following decitabine or DMSO in combination with CD33 (CD8) CAR or mock T cells. RAJI cell line was used as a negative control.
Figure 9B:
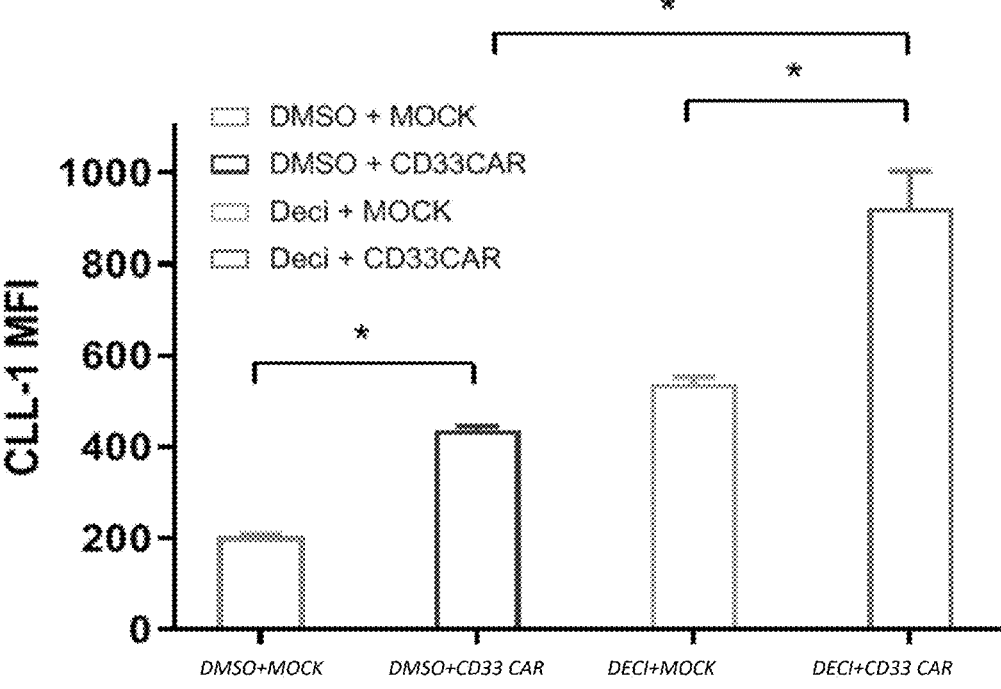

We further detected MFI of PD-L1 and CLL-1 expression on residual AML cells that survived the treatment with decitabine in combination with CD33 CAR T cells. Expression levels of PD-L1 (FIG. 9A) and CLL-1 (FIG. 9B) were significantly increased following combinational treatment in vitro.

Figure 10:
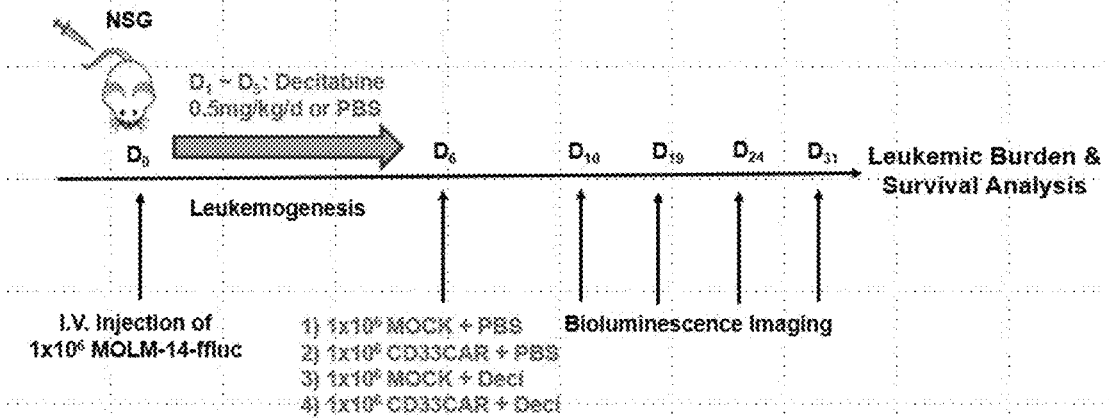
FIG. 10 shows a representative in vivo study using a NSG xenograft model with MOLM-14-ffluc that received decitabine in combination with CD33 CAR T cell therapies.

Example 7: Decitabine Improves the Antileukemic Efficacy of CD33 CAR T Cells In Vivo NSG mice were i.v. injected with $1 \times 10^6$ MOLM-14-ffluc cells on Day 0. From day 1 to 5, they were administered with 0.5 mg/kg/d decitabine or PBS by intraperitoneal (i.p.) injection for 5 consecutive days. On day 6, mice were administered with $1 \times 10^6$ CD33 (CD8) CAR (SEQ ID NO: 30) or mock T cells by i.v. injection (FIG. 10).

Figure 11A:
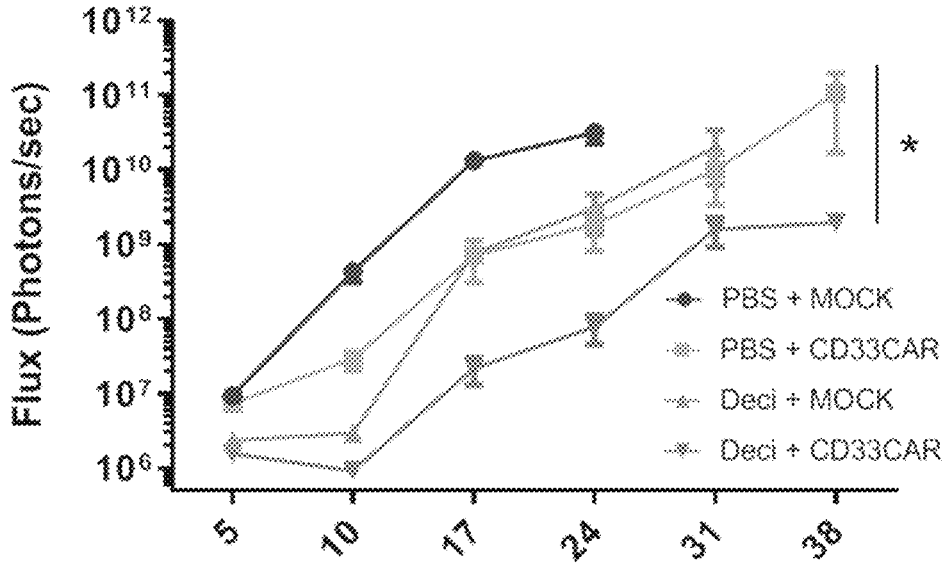
FIGS. 11A-11B show the results of combinational efficacies of decitabine and CD33 (CD8) CART cells in vivo.
Figure 11B:
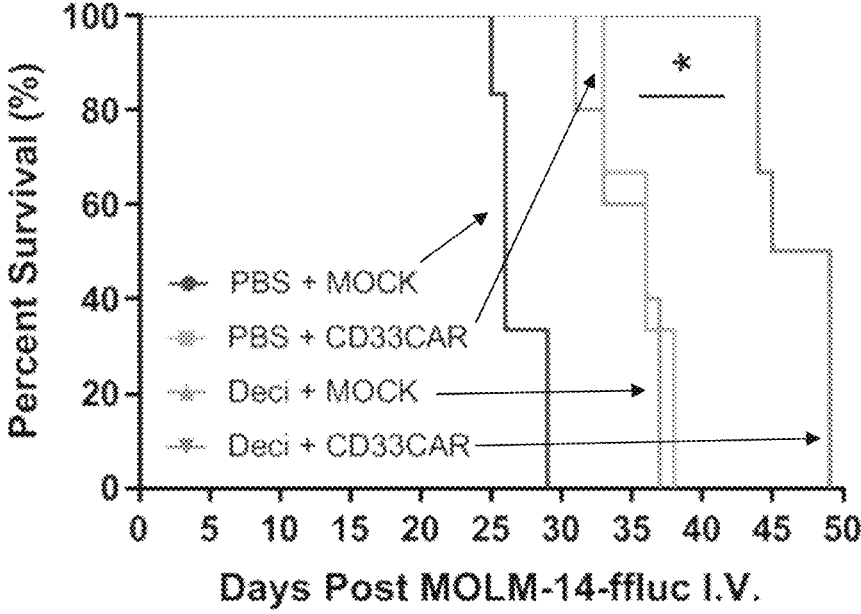

Consistent with in vitro findings, decitabine in combination with CD33 CAR T cells significantly reduced leukemic burden (FIG. 11A) and prolonged overall survival (FIG. 11B) in vivo.

Example 8: PD-1/PD-L1 Blockade Enhances CD33 CAR T Cell Efficacy

Figure 12:
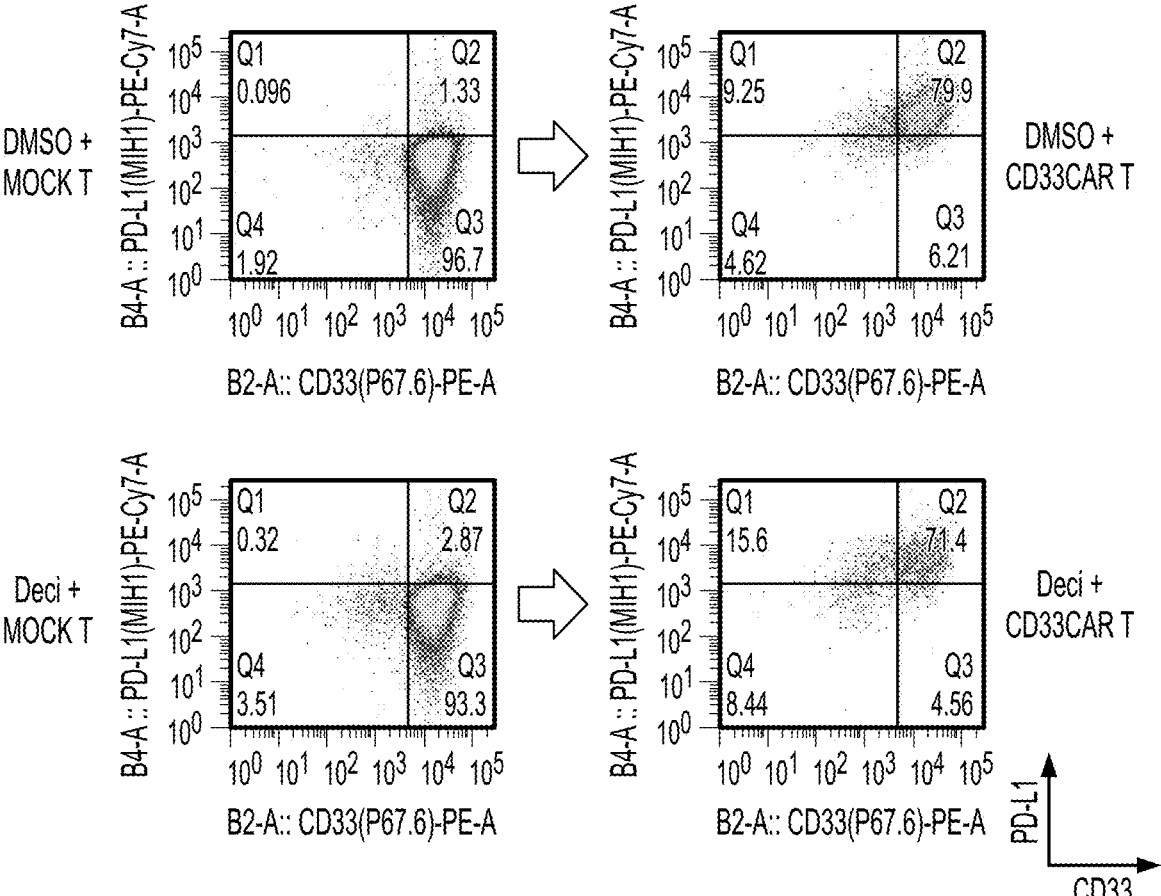
FIG. 12 shows residual AML cells that survived the treatment with 10 nM decitabine and 1:50 E:T ratio of CD33 (CD8) CART cells significantly increased PD-L1 expression levels.
Figure 13:
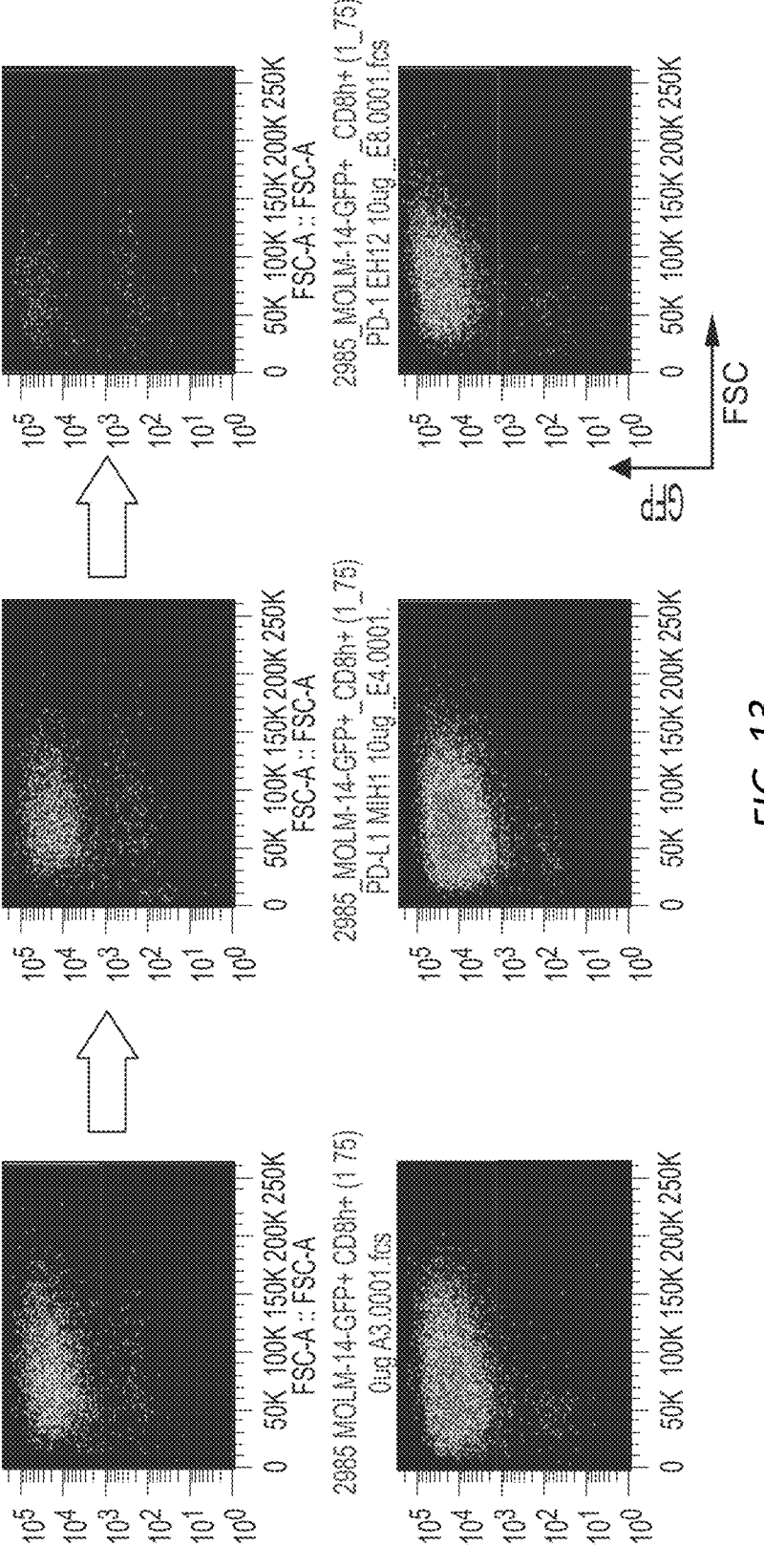
FIG. 13 shows anti-PD-1 antibody (10 μg/mL) significantly enhanced the anti-AML efficacy of CD33 (CD8) CART cells at an E:T ratio of 1:75.

Checkpoint blockade targeting programmed death-1 (PD-1)/PD-L1 has been involved in resistance mechanisms to immune-based therapies. Residual AML cells that survived the treatment with 10 nM decitabine and 1:50 E:T ratio of CD33 (CD8) CAR (SEQ ID NO: 30) T cells exhibited significantly elevated PD-L1 expression (FIG. 12). It was found that anti-PD-1 antibody (10 μg/mL) significantly enhanced the anti-AML efficacy of CD33 (CD8) CAR (SEQ ID NO: 30) T cells at an E:T ratio of 1:75 (FIG. 13).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All references are herein incorporated in their entirety for any and all purposes.

---

What is claimed is:

1. A nucleic acid molecule encoding a polypeptide comprising a chimeric antigen receptor (CAR), wherein the CAR comprises the amino acid sequence of SEQ ID NO: 30 or the amino acid sequence of SEQ ID NO: 31.

2. An expression vector or a viral vector comprising the nucleic acid molecule of claim 1.

3. A population of human immune cells transduced by a vector comprising the nucleic acid molecule of claim 1.

4. The population of human immune cells of claim 3, wherein the population of human immune cells comprise central memory T cells, naive memory T cells, pan T cells, NK cells, or PBMCs substantially depleted for CD25+ cells and CD14+ cells.

5. A method of preparing CD33 CAR T cells comprising: providing a population of autologous or allogeneic human T cells and transducing the T cells with a vector comprising the nucleic acid molecule of claim 1.

6. A population of human immune cells harboring the nucleic acid molecule of claim 1.

7. The nucleic acid molecule of claim 1, wherein the CAR consists of the amino acid sequence of SEQ ID NO:30 or the amino acid sequence of SEQ ID NO:31.

* * * * *

```
                      SEQUENCE LISTING

<160> NUMBER OF SEQ ID NOS: 38

<210> SEQ ID NO 1
<211> LENGTH: 242
<212> TYPE: PRT
<213> ORGANISM: Artificial Sequence
<220> FEATURE:
<223> OTHER INFORMATION: CD33 scFv

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
            35                  40                  45

Gly Tyr Ile Tyr Pro Tyr Asn Gly Gly Thr Gly Tyr Asn Gln Lys Phe
        50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Asp Ile Gln Met Thr Gln Ser Pro Ser Ser Leu Ser Ala
        130                 135                 140

Ser Val Gly Asp Arg Val Thr Ile Thr Cys Arg Ala Ser Glu Ser Val
145                 150                 155                 160

Asp Asn Tyr Gly Ile Ser Phe Met Asn Trp Phe Gln Gln Lys Pro Gly
            165                 170                 175

Lys Ala Pro Lys Leu Leu Ile Tyr Ala Ala Ser Asn Gln Gly Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Asp Asp Phe Ala Thr Tyr Tyr Cys Gln
        210                 215                 220

Gln Ser Lys Glu Val Pro Trp Thr Phe Gly Gln Gly Thr Lys Val Glu
225                 230                 235                 240

Ile Lys

<210> SEQ ID NO 2
<211> LENGTH: 10
<212> TYPE: PRT
<213> ORGANISM: Artificial Sequence
<220> FEATURE:
<223> OTHER INFORMATION: linker
```

```
<400> SEQUENCE: 2

Gly Gly Gly Ser Ser Gly Gly Gly Ser Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: IgG4 hinge (S to P) (S228P)

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: IgG4 hinge

<400> SEQUENCE: 4

Glu Ser Lys Tyr Gly Pro Pro Cys Pro Ser Cys Pro
1               5                   10

<210> SEQ ID NO 5
<211> LENGTH: 22
<212> TYPE: PRT
<213> ORGANISM: Artificial Sequence
<220> FEATURE:
<223> OTHER INFORMATION: IgG4 hinge (S228P)+ linker

<400> SEQUENCE: 5

Glu Ser Lys Tyr Gly Pro Pro Cys Pro Pro Cys Pro Gly Gly Gly Ser
1               5                   10                  15

Ser Gly Gly Gly Ser Gly
            20

<210> SEQ ID NO 6
<211> LENGTH: 39
<212> TYPE: PRT
<213> ORGANISM: Artificial Sequence
<220> FEATURE:
<223> OTHER INFORMATION: CD28 hinge

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 48
<212> TYPE: PRT
<213> ORGANISM: Artificial Sequence
<220> FEATURE:
<223> OTHER INFORMATION: CD8 hinge-48aa

<400> SEQUENCE: 7

Ala Lys Pro Thr Thr Thr Pro Ala Pro Arg Pro Pro Thr Pro Ala Pro
1               5                   10                  15
```

-continued

```
Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

<210> SEQ ID NO 8
<211> LENGTH: 45
<212> TYPE: PRT
<213> ORGANISM: Artificial Sequence
<220> FEATURE:
<223> OTHER INFORMATION: CD8 hinge-45aa

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 9
<211> LENGTH: 129
<212> TYPE: PRT
<213> ORGANISM: Artificial Sequence
<220> FEATURE:
<223> OTHER INFORMATION: IgG4(HL-CH3) (includes S228P in hinge)

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
            35                  40                  45

Cys Leu Val Lys Gly Phe Tyr Pro Ser Asp Ile Ala Val Glu Trp Glu
        50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 10
<211> LENGTH: 229
<212> TYPE: PRT
<213> ORGANISM: Artificial Sequence
<220> FEATURE:
<223> OTHER INFORMATION: IgG4(L235E,N297Q)

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30
```

-continued

Leu Met Ile Ser Arg Thr Pro Glu Val Thr Cys Val Val Val Asp Val
      35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 229
<212> TYPE: PRT
<213> ORGANISM: Artificial Sequence
<220> FEATURE:
<223> OTHER INFORMATION: IgG4(S228P, L235E, N297Q)

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
      35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

```
Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 107
<212> TYPE: PRT
<213> ORGANISM: Artificial Sequence
<220> FEATURE:
<223> OTHER INFORMATION: IgG4(CH3)

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65              70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Artificial Sequence
<220> FEATURE:
<223> OTHER INFORMATION: CD3z

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 14
<211> LENGTH: 27
<212> TYPE: PRT
<213> ORGANISM: Artificial Sequence
<220> FEATURE:
<223> OTHER INFORMATION: CD28

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 15
<211> LENGTH: 28
<212> TYPE: PRT
<213> ORGANISM: Artificial Sequence
<220> FEATURE:
<223> OTHER INFORMATION: CD28(M)

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Artificial Sequence
<220> FEATURE:
<223> OTHER INFORMATION: CD4

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Artificial Sequence
<220> FEATURE:
<223> OTHER INFORMATION: CD8tm

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 18
<211> LENGTH: 23
<212> TYPE: PRT
<213> ORGANISM: Artificial Sequence
<220> FEATURE:
<223> OTHER INFORMATION: CD8tm2

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19
<211> LENGTH: 24
<212> TYPE: PRT
<213> ORGANISM: Artificial Sequence
<220> FEATURE:
<223> OTHER INFORMATION: CD8tm3

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20

-continued

```
<210> SEQ ID NO 20
<211> LENGTH: 27
<212> TYPE: PRT
<213> ORGANISM: Artificial Sequence
<220> FEATURE:
<223> OTHER INFORMATION: 41BB

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 21
<211> LENGTH: 112
<212> TYPE: PRT
<213> ORGANISM: Artificial Sequence
<220> FEATURE:
<223> OTHER INFORMATION: CD3

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 41
<212> TYPE: PRT
<213> ORGANISM: Artificial Sequence
<220> FEATURE:
<223> OTHER INFORMATION: CD28

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 23
<211> LENGTH: 41
<212> TYPE: PRT
<213> ORGANISM: Artificial Sequence
<220> FEATURE:
<223> OTHER INFORMATION: CD28gg*

<400> SEQUENCE: 23

Arg Ser Lys Arg Ser Arg Gly Gly His Ser Asp Tyr Met Asn Met Thr
1               5                   10                  15
```

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 24
<211> LENGTH: 42
<212> TYPE: PRT
<213> ORGANISM: Artificial Sequence
<220> FEATURE:
<223> OTHER INFORMATION: 41BB

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 25
<211> LENGTH: 42
<212> TYPE: PRT
<213> ORGANISM: Artificial Sequence
<220> FEATURE:
<223> OTHER INFORMATION: OX40

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
            35                  40

<210> SEQ ID NO 26
<211> LENGTH: 323
<212> TYPE: PRT
<213> ORGANISM: Artificial Sequence
<220> FEATURE:
<223> OTHER INFORMATION: truncated CD19R

<400> SEQUENCE: 26

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

-continued

```
Leu Gly Gly Leu Gly Cys Gly Leu Lys Asn Arg Ser Ser Glu Gly Pro
    130             135             140

Ser Ser Pro Ser Gly Lys Leu Met Ser Pro Lys Leu Tyr Val Trp Ala
145             150             155             160

Lys Asp Arg Pro Glu Ile Trp Glu Gly Glu Pro Pro Cys Val Pro Pro
                165             170             175

Arg Asp Ser Leu Asn Gln Ser Leu Ser Gln Asp Leu Thr Met Ala Pro
            180             185             190

Gly Ser Thr Leu Trp Leu Ser Cys Gly Val Pro Pro Asp Ser Val Ser
            195             200             205

Arg Gly Pro Leu Ser Trp Thr His Val His Pro Lys Gly Pro Lys Ser
    210             215             220

Leu Leu Ser Leu Glu Leu Lys Asp Asp Arg Pro Ala Arg Asp Met Trp
225             230             235             240

Val Met Glu Thr Gly Leu Leu Leu Pro Arg Ala Thr Ala Gln Asp Ala
            245             250             255

Gly Lys Tyr Tyr Cys His Arg Gly Asn Leu Thr Met Ser Phe His Leu
            260             265             270

Glu Ile Thr Ala Arg Pro Val Leu Trp His Trp Leu Leu Arg Thr Gly
            275             280             285

Gly Trp Lys Val Ser Ala Val Thr Leu Ala Tyr Leu Ile Phe Cys Leu
    290             295             300

Cys Ser Leu Val Gly Ile Leu His Leu Gln Arg Ala Leu Val Leu Arg
305             310             315             320

Arg Lys Arg

<210> SEQ ID NO 27
<211> LENGTH: 24
<212> TYPE: PRT
<213> ORGANISM: Artificial Sequence
<220> FEATURE:
<223> OTHER INFORMATION: ribosomal skip sequence

<400> SEQUENCE: 27

Leu Glu Gly Gly Gly Glu Gly Arg Gly Ser Leu Leu Thr Cys Gly Asp
1               5               10              15

Val Glu Glu Asn Pro Gly Pro Arg
            20

<210> SEQ ID NO 28
<211> LENGTH: 354
<212> TYPE: PRT
<213> ORGANISM: Artificial Sequence
<220> FEATURE:
<223> OTHER INFORMATION: truncated EGFR

<400> SEQUENCE: 28

Leu Val Thr Ser Leu Leu Leu Cys Glu Leu Pro His Pro Ala Phe Leu
1               5               10              15

Leu Ile Pro Arg Lys Val Cys Asn Gly Ile Gly Ile Gly Glu Phe Lys
            20              25              30

Asp Ser Leu Ser Ile Asn Ala Thr Asn Ile Lys His Phe Lys Asn Cys
        35              40              45

Thr Ser Ile Ser Gly Asp Leu His Ile Leu Pro Val Ala Phe Arg Gly
    50              55              60

Asp Ser Phe Thr His Thr Pro Pro Leu Asp Pro Gln Glu Leu Asp Ile
65              70              75              80
```

-continued

```
Leu Lys Thr Val Lys Glu Ile Thr Gly Phe Leu Leu Ile Gln Ala Trp
            85                  90                  95

Pro Glu Asn Arg Thr Asp Leu His Ala Phe Glu Asn Leu Glu Ile Ile
            100                 105                 110

Arg Gly Arg Thr Lys Gln His Gly Gln Phe Ser Leu Ala Val Val Ser
            115                 120                 125

Leu Asn Ile Thr Ser Leu Gly Leu Arg Ser Leu Lys Glu Ile Ser Asp
    130                 135                 140

Gly Asp Val Ile Ile Ser Gly Asn Lys Asn Leu Cys Tyr Ala Asn Thr
145                 150                 155                 160

Ile Asn Trp Lys Lys Leu Phe Gly Thr Ser Gly Gln Lys Thr Lys Ile
                165                 170                 175

Ile Ser Asn Arg Gly Glu Asn Ser Cys Lys Ala Thr Gly Gln Val Cys
                180                 185                 190

His Ala Leu Cys Ser Pro Glu Gly Cys Trp Gly Pro Glu Pro Arg Asp
            195                 200                 205

Cys Val Ser Cys Arg Asn Val Ser Arg Gly Arg Glu Cys Val Asp Lys
    210                 215                 220

Cys Asn Leu Leu Glu Gly Glu Pro Arg Glu Phe Val Glu Asn Ser Glu
225                 230                 235                 240

Cys Ile Gln Cys His Pro Glu Cys Leu Pro Gln Ala Met Asn Ile Thr
                245                 250                 255

Cys Thr Gly Arg Gly Pro Asp Asn Cys Ile Gln Cys Ala His Tyr Ile
                260                 265                 270

Asp Gly Pro His Cys Val Lys Thr Cys Pro Ala Gly Val Met Gly Glu
            275                 280                 285

Asn Asn Thr Leu Val Trp Lys Tyr Ala Asp Ala Gly His Val Cys His
    290                 295                 300

Leu Cys His Pro Asn Cys Thr Tyr Gly Cys Thr Gly Pro Gly Leu Glu
305                 310                 315                 320

Gly Cys Pro Thr Asn Gly Pro Lys Ile Pro Ser Ile Ala Thr Gly Met
                325                 330                 335

Val Gly Ala Leu Leu Leu Leu Leu Val Val Ala Leu Gly Ile Gly Leu
                340                 345                 350

Phe Met

<210> SEQ ID NO 29

<400> SEQUENCE: 29

000

<210> SEQ ID NO 30
<211> LENGTH: 468
<212> TYPE: PRT
<213> ORGANISM: Artificial Sequence
<220> FEATURE:
<223> OTHER INFORMATION: CD33 CD8 CAR

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
            35                  40                  45
```

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Gly Gly Gly Ser Gly Gly Gly Ser Gly Gly
            115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Lys Ala Pro Lys Leu Leu Ile Tyr Ala Ala Ser Asn Gln Gly Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Asp Asp Phe Ala Thr Tyr Tyr Cys Gln
    210                 215                 220

Gln Ser Lys Glu Val Pro Trp Thr Phe Gly Gln Gly Thr Lys Val Glu
225                 230                 235                 240

Ile Lys Thr Thr Thr Pro Ala Pro Arg Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
            275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Gly Gly Gly Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

```
Leu Ser Thr Ala Thr Lys Asp Thr Tyr Asp Ala Leu His Met Gln Ala
    450             455             460

Leu Pro Pro Arg
465

<210> SEQ ID NO 31
<211> LENGTH: 650
<212> TYPE: PRT
<213> ORGANISM: Artificial Sequence
<220> FEATURE:
<223> OTHER INFORMATION: CD33 EQ CAR

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Asp Ile Gln Met Thr Gln Ser Pro Ser Ser Leu Ser Ala
        130                 135                 140

Ser Val Gly Asp Arg Val Thr Ile Thr Cys Arg Ala Ser Glu Ser Val
145                 150                 155                 160

Asp Asn Tyr Gly Ile Ser Phe Met Asn Trp Phe Gln Gln Lys Pro Gly
            165                 170                 175

Lys Ala Pro Lys Leu Leu Ile Tyr Ala Ala Ser Asn Gln Gly Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Asp Asp Phe Ala Thr Tyr Tyr Cys Gln
    210                 215                 220

Gln Ser Lys Glu Val Pro Trp Thr Phe Gly Gln Gly Thr Lys Val Glu
225                 230                 235                 240

Ile Lys Glu Ser Lys Tyr Gly Pro Pro Cys Pro Pro Cys Pro Ala Pro
                245                 250                 255

Glu Phe Glu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser Gln Glu Asp Pro Glu Val Gln Phe Asn Trp Tyr Val Asp
            290                 295                 300

Gly Val Glu Val His Asn Ala Lys Thr Lys Pro Arg Glu Glu Gln Phe
305                 310                 315                 320

Gln Ser Thr Tyr Arg Val Val Ser Val Leu Thr Val Leu His Gln Asp
                325                 330                 335
```

-continued

```
Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
            355                 360                 365

Glu Pro Gln Val Tyr Thr Leu Pro Pro Ser Gln Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
            435                 440                 445

Cys Ser Val Met His Glu Ala Leu His Asn His Tyr Thr Gln Lys Ser
    450                 455                 460

Leu Ser Leu Ser Leu Gly Lys Met Ala Leu Ile Val Leu Gly Gly Val
465                 470                 475                 480

Ala Gly Leu Leu Leu Phe Ile Gly Leu Gly Ile Phe Phe Lys Arg Gly
                485                 490                 495

Arg Lys Lys Leu Leu Tyr Ile Phe Lys Gln Pro Phe Met Arg Pro Val
            500                 505                 510

Gln Thr Thr Gln Glu Glu Asp Gly Cys Ser Cys Arg Phe Pro Glu Glu
            515                 520                 525

Glu Glu Gly Gly Cys Glu Leu Gly Gly Gly Arg Val Lys Phe Ser Arg
    530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
            595                 600                 605

Tyr Ser Glu Ile Gly Met Lys Gly Glu Arg Arg Arg Gly Lys Gly His
    610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 32
<211> LENGTH: 116
<212> TYPE: PRT
<213> ORGANISM: Artificial Sequence
<220> FEATURE:
<223> OTHER INFORMATION: CD33 V1

<400> SEQUENCE: 32

Gln Val Gln Leu Val Gln Ser Gly Ala Glu Val Lys Lys Pro Gly Ser
1                 5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
            35                  40                  45
```

```
Gly Tyr Ile Tyr Pro Tyr Asn Gly Gly Thr Gly Tyr Asn Gln Lys Phe
    50              55              60
```

```
Lys Ser Lys Ala Thr Ile Thr Ala Asp Glu Ser Thr Asn Thr Ala Tyr
65              70              75              80
```

```
Met Glu Leu Ser Ser Leu Arg Ser Glu Asp Thr Ala Val Tyr Tyr Cys
                85              90              95
```

```
Ala Arg Gly Arg Pro Ala Met Asp Tyr Trp Gly Gln Gly Thr Leu Val
            100             105             110
```

```
Thr Val Ser Ser
        115
```

```
<210> SEQ ID NO 33
<211> LENGTH: 112
<212> TYPE: PRT
<213> ORGANISM: Artificial Sequence
<220> FEATURE:
<223> OTHER INFORMATION: CD33 Vh
```

```
<400> SEQUENCE: 33
```

```
Asp Ile Val Met Thr Gln Ser Pro Asp Ser Leu Ala Val Ser Leu Gly
1               5               10              15
```

```
Glu Arg Ala Thr Met Ser Cys Lys Ser Ser Gln Ser Ile Leu Tyr Ser
            20              25              30
```

```
Ser Asn Gln Lys Asn Tyr Leu Ala Trp Tyr Gln Lys Pro Gly Gln
        35              40              45
```

```
Ser Pro Lys Leu Leu Ile Tyr Trp Ala Ser Thr Arg Glu Ser Gly Val
    50              55              60
```

```
Pro Asp Arg Phe Ser Gly Ser Gly Ser Gly Thr Asp Phe Thr Leu Thr
65              70              75              80
```

```
Ile Ser Ser Leu Gln Ala Glu Asp Val Ala Val Tyr Tyr Cys His Gln
                85              90              95
```

```
Tyr Leu Ser Ser Tyr Thr Phe Gly Gln Gly Thr Lys Leu Glu Ile Lys
            100             105             110
```

```
<210> SEQ ID NO 34
<211> LENGTH: 22
<212> TYPE: PRT
<213> ORGANISM: Artificial Sequence
<220> FEATURE:
<223> OTHER INFORMATION: GMCSFRa signal sequence
```

```
<400> SEQUENCE: 34
```

```
Met Leu Leu Leu Val Thr Ser Leu Leu Leu Cys Glu Leu Pro His Pro
1               5               10              15
```

```
Ala Phe Leu Leu Ile Pro
            20
```

```
<210> SEQ ID NO 35
<211> LENGTH: 2616
<212> TYPE: DNA
<213> ORGANISM: Artificial Sequence
<220> FEATURE:
<223> OTHER INFORMATION: CD33 CD8 CAR preceded by a GMCSR signal
      sequence and followed by a T2A skip sequence and EGFRt
```

```
<400> SEQUENCE: 35
```

```
atgctgctcc ttgtcacatc cctgctgctg tgcgaactgc cacatcccgc cttcctgctg      60
```

```
atccccaag tgcagctcgt gcagtccgga gccgaagtca agaagcctgg cagctccgtc     120
```

```
aaggtgtcct gcaaagcctc cggctacacc tttaccgact acaacatgca ctgggtccgc     180
```

-continued

```
caagcacctg gacagggact ggagtggatt gggtacatct acccttacaa cggaggcacc      240
gggtacaacc agaagttcaa gtcgaaggcc accattaccg cggacgaatc caccaacacc      300
gcgtatatgg agctctcatc cttgcggtcg gaggacactg ccgtgtacta ctgcgcgagg      360
ggtagaccgg caatggacta ctggggccag ggcactctcg tcaccgtgtc ctctggtggt      420
ggaggctcag gaggaggggg atccggtgga ggagggagcg atatccagat gacgcagtca      480
ccctcgtccc tgagcgcttc cgtgggcgat cgcgtgacta tcacttgccg ggcttccgag      540
tccgtggata actacggaat ttcctttatg aactggttcc agcaaaagcc gggaaaggcc      600
ccaaagctcc tgatctacgc cgccagcaat cagggatcgg gagtgccctc acggttctcc      660
gggagcggtt caggcaccga cttcaccctt actatttcga gcctgcaacc tgacgatttc      720
gccacttatt actgccaaca gtccaaggaa gtgccgtgga cgttcggcca ggggaccaag      780
gtggaaatca gaccacgac gccagcgccg cgaccaccaa caccggcgcc caccatcgcg      840
tcgcagcccc tgtccctgcg cccagaggcg tgccggccag cggcggggggg cgcagtgcac      900 acgagggggc tggacttcgc ctgtgatatc tacatctggg cgcccttggc cgggacttgt      960
ggggtccttc tcctgtcact ggttatcacc ctttactgca agcggggcag aaagaagctg     1020
ctgtacatct tcaagcagcc cttcatgcgg cccgtgcaga ccacccagga agaggacggc     1080
tgcagctgcc ggttccccga ggaagaggaa ggcggctgcg agctgggagg cggcagagtg     1140
aagttcagcc ggtccgccga cgcccctgcc taccagcagg gccagaacca gctgtacaac     1200
gagctgaacc tgggcaggcg ggaggaatac gacgtgctgg acaagcggag aggccgggac     1260
cctgagatgg gcggcaagcc caggcggaag aaccctcagg aaggcctgta taacgaactg     1320
cagaaagaca gatggccgga ggcctacagc gagatcggca tgaagggcga gcggcggagg     1380
ggcaagggcc acgacggcct gtaccagggc ctgagcaccg ccaccaagga tacctacgac     1440
gccctgcaca tgcaggccct gcccccaagg ctcgagggcg cggagagggg cagaggaagt     1500
cttctaacat gcggtgacgt ggaggagaat cccggcccta ggatgcttct cctggtgaca     1560
agccttctgc tctgtgagtt accacaccca gcattcctcc tgatcccacg caaagtgtgt     1620
aacggaatag gtattggtga atttaaagac tcactctcca taaatgctac gaatattaaa     1680
cacttcaaaa actgcacctc catcagtggc gatctccaca tcctgccggt ggcatttagg     1740
ggtgactcct tcacacatac tcctcctctg gatccacagg aactggatat tctgaaaacc     1800
gtaaaggaaa tcacagggtt tttgctgatt caggcttggc ctgaaaacag gacggacctc     1860
catgcctttg agaacctaga aatcatacgc ggcaggacca gcaacatgg tcagttttct     1920 cttgcagtcg tcagcctgaa cataacatcc ttgggattac gctccctcaa ggagataagt     1980 gatgagatg tgataatttc aggaaacaaa aatttgtgct atgcaaatac aataaactgg     2040
aaaaaactgt ttgggacctc cggtcagaaa accaaaatta taagcaacag aggtgaaaac     2100
agctgcaagg ccacaggcca ggtctgccat gccttgtgct cccccgaggg ctgctggggc     2160
ccggagccca gggactgcgt ctcttgccgg aatgtcagcc gaggcaggga atgcgtggac     2220
aagtgcaacc ttctggaggg tgagccaagg gagtttgtgg agaactctga gtgcatacag     2280
tgccacccag agtgcctgcc tcaggccatg aacatcacct gcacaggacg gggaccagac     2340
aactgtatcc agtgtgccca ctacattgac ggccccccact gcgtcaagac ctgcccggca     2400
ggagtcatgg gagaaaacaa caccctggtc tggaagtacg cagacgccgg ccatgtgtgc     2460
cacctgtgcc atccaaactg cacctacgga tgcactgggc caggtcttga aggctgtcca     2520
```

-continued

```
acgaatgggc ctaagatccc gtccatcgcc actgggatgg tggggggccct cctcttgctg    2580 ctggtggtgg ccctggggat cggcctcttc atgtga                               2616
```

<210> SEQ ID NO 36
<211> LENGTH: 871
<212> TYPE: PRT
<213> ORGANISM: Artificial Sequence
<220> FEATURE:
<223> OTHER INFORMATION: CD33 CD8 CAR preceded by a GMCSR signal
      sequence and followed by a T2A skip sequence and EGFRt

<400> SEQUENCE: 36

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Tyr Thr Phe Thr Asp Tyr Asn Met His Trp Val Arg Gln Ala Pro Gly
    50                  55                  60

Gln Gly Leu Glu Trp Ile Gly Tyr Ile Tyr Pro Tyr Asn Gly Gly Thr
65                  70                  75                  80

Gly Tyr Asn Gln Lys Phe Lys Ser Lys Ala Thr Ile Thr Ala Asp Glu
                85                  90                  95

Ser Thr Asn Thr Ala Tyr Met Glu Leu Ser Ser Leu Arg Ser Glu Asp
            100                 105                 110

Thr Ala Val Tyr Tyr Cys Ala Arg Gly Arg Pro Ala Met Asp Tyr Trp
            115                 120                 125

Gly Gln Gly Thr Leu Val Thr Val Ser Ser Gly Gly Gly Gly Ser Gly
        130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Glu Ser Val Asp Asn Tyr Gly Ile Ser Phe Met Asn Trp
            180                 185                 190

Phe Gln Gln Lys Pro Gly Lys Ala Pro Lys Leu Leu Ile Tyr Ala Ala
            195                 200                 205

Ser Asn Gln Gly Ser Gly Val Pro Ser Arg Phe Ser Gly Ser Gly Ser
        210                 215                 220

Gly Thr Asp Phe Thr Leu Thr Ile Ser Ser Leu Gln Pro Asp Asp Phe
225                 230                 235                 240

Ala Thr Tyr Tyr Cys Gln Gln Ser Lys Glu Val Pro Trp Thr Phe Gly
                245                 250                 255

Gln Gly Thr Lys Val Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
        290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335
```

-continued

```
Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Gly Gly Gly Arg Val Lys Phe Ser Arg
        370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
        450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg Leu Glu Gly Gly Gly Glu
                485                 490                 495

Gly Arg Gly Ser Leu Leu Thr Cys Gly Asp Val Glu Glu Asn Pro Gly
            500                 505                 510

Pro Arg Met Leu Leu Leu Val Thr Ser Leu Leu Leu Cys Glu Leu Pro
            515                 520                 525

His Pro Ala Phe Leu Leu Ile Pro Arg Lys Val Cys Asn Gly Ile Gly
        530                 535                 540

Ile Gly Glu Phe Lys Asp Ser Leu Ser Ile Asn Ala Thr Asn Ile Lys
545                 550                 555                 560

His Phe Lys Asn Cys Thr Ser Ile Ser Gly Asp Leu His Ile Leu Pro
                565                 570                 575

Val Ala Phe Arg Gly Asp Ser Phe Thr His Thr Pro Pro Leu Asp Pro
            580                 585                 590

Gln Glu Leu Asp Ile Leu Lys Thr Val Lys Glu Ile Thr Gly Phe Leu
            595                 600                 605

Leu Ile Gln Ala Trp Pro Glu Asn Arg Thr Asp Leu His Ala Phe Glu
        610                 615                 620

Asn Leu Glu Ile Ile Arg Gly Arg Thr Lys Gln His Gly Gln Phe Ser
625                 630                 635                 640

Leu Ala Val Val Ser Leu Asn Ile Thr Ser Leu Gly Leu Arg Ser Leu
                645                 650                 655

Lys Glu Ile Ser Asp Gly Asp Val Ile Ile Ser Gly Asn Lys Asn Leu
            660                 665                 670

Cys Tyr Ala Asn Thr Ile Asn Trp Lys Lys Leu Phe Gly Thr Ser Gly
        675                 680                 685

Gln Lys Thr Lys Ile Ile Ser Asn Arg Gly Glu Asn Ser Cys Lys Ala
        690                 695                 700

Thr Gly Gln Val Cys His Ala Leu Cys Ser Pro Glu Gly Cys Trp Gly
705                 710                 715                 720

Pro Glu Pro Arg Asp Cys Val Ser Cys Arg Asn Val Ser Arg Gly Arg
                725                 730                 735

Glu Cys Val Asp Lys Cys Asn Leu Leu Glu Gly Glu Pro Arg Glu Phe
            740                 745                 750
```

-continued

```
Val Glu Asn Ser Glu Cys Ile Gln Cys His Pro Glu Cys Leu Pro Gln
        755                 760                 765

Ala Met Asn Ile Thr Cys Thr Gly Arg Gly Pro Asp Asn Cys Ile Gln
        770                 775                 780

Cys Ala His Tyr Ile Asp Gly Pro His Cys Val Lys Thr Cys Pro Ala
785                 790                 795                 800

Gly Val Met Gly Glu Asn Asn Thr Leu Val Trp Lys Tyr Ala Asp Ala
                805                 810                 815

Gly His Val Cys His Leu Cys His Pro Asn Cys Thr Tyr Gly Cys Thr
            820                 825                 830

Gly Pro Gly Leu Glu Gly Cys Pro Thr Asn Gly Pro Lys Ile Pro Ser
        835                 840                 845

Ile Ala Thr Gly Met Val Gly Ala Leu Leu Leu Leu Leu Val Val Ala
    850                 855                 860

Leu Gly Ile Gly Leu Phe Met
865                 870

<210> SEQ ID NO 37
<211> LENGTH: 3162
<212> TYPE: DNA
<213> ORGANISM: Artificial Sequence
<220> FEATURE:
<223> OTHER INFORMATION: CD33 EQ CAR preceded by a GMCSR signal sequence
      and followed by a T2A skip sequence and EGFRt

<400> SEQUENCE: 37
atgctgctcc ttgtcacatc cctgctgctg tgcgaactgc cacatcccgc cttcctgctg      60
atcccccaag tgcagctcgt gcagtccgga gccgaagtca agaagcctgg cagctccgtc     120
aaggtgtcct gcaaagcctc cggctacacc tttaccgact acaacatgca ctgggtccgc     180
caagcacctg gacagggact ggagtggatt gggtacatct accctttacaa cggaggcacc     240 gggtacaacc agaagttcaa gtcgaaggcc accattaccg cggacgaatc caccaacacc     300
gcgtatatgg agctctcatc cttgcggtcg gaggacactg ccgtgtacta ctgcgcgagg     360
ggtagaccgg caatggacta ctggggccag ggcactctcg tcaccgtgtc ctctggtggt     420
ggaggctcag gaggagggggg atccggtgga ggagggagcg atatccagat gacgcagtca     480
ccctcgtccc tgagcgcttc cgtgggcgat cgcgtgacta tcacttgccg ggcttccgag     540
tccgtggata actacggaat ttcctttatg aactggttcc agcaaaagcc gggaaaggcc     600
ccaaagctcc tgatctacgc cgccagcaat cagggatcgg gagtgccctc acggttctcc     660
gggagcggtt caggcaccga cttcaccctt actatttcga gcctgcaacc tgacgatttc     720
gccacttatt actgccaaca gtccaaggaa gtgccgtgga cgttcggcca ggggaccaag     780
gtggaaatca aggagagcaa atacggaccg ccgtgtccac cctgtcctgc acccgagttc     840
gaaggcggcc cttccgtgtt cctgttcccg ccgaagccca aggacaccct gatgatctcg     900 agaacccccgg aggtgacctg cgtggtggtg acgtgtcccc aggaagatcc cgaggtccag     960
ttcaattggt acgtggacgg cgtggaagtg cacaatgcca agaccaagcc cagagaggaa    1020
cagttccaaa gcacctaccg ggtggtgtcc gtgctgaccg tgctgcacca ggactggctg    1080
aacggcaaag agtacaagtg caaggtgtcc aacaagggcc tgcccagcag catcgagaaa    1140
accatcagca aggccaaggg ccagccccgc gagccccagg tgtacacact gcccccccagc    1200 caggaagaga tgaccaagaa ccaggtgtcc ctgacctgcc tggtcaaggg cttctacccc    1260
agcgatatcg ccgtggaatg ggagagcaac ggccagcccg agaacaacta caagaccacc    1320
```

-continued

```
ccccctgtgc tggacagcga cggcagcttc ttcctgtact cccggctgac cgtggacaag   1380
agccggtggc aggaaggcaa cgtcttcagc tgcagcgtga tgcacgaggc cctgcacaac   1440
cactacaccc agaagtctct gagcctgagc ctgggcaaga tggccctgat cgtgctgggc   1500
ggagtggccg gactgctgct gtttatcggc ctgggcatct tcttcaagcg gggcagaaag   1560
aagctgctgt acatcttcaa gcagcccttc atgcggcccg tgcagaccac ccaggaagag   1620
gacggctgca gctgccggtt ccccgaggaa gaggaaggcg gctgcgagct gggaggcggc   1680
agagtgaagt tcagccggtc cgccgacgcc cctgcctacc agcagggcca gaaccagctg   1740
tacaacgagc tgaacctggg caggcgggag gaatacgacg tgctggacaa gcggagaggc   1800
cgggaccctg agatgggcgg caagcccagg cggaagaacc ctcaggaagg cctgtataac   1860
gaactgcaga agacaagat ggccgaggcc tacagcgaga tcggcatgaa gggcgagcgg   1920
cggaggggca agggccacga cggcctgtac cagggcctga gcaccgccac caaggatacc   1980
tacgacgccc tgcacatgca ggccctgccc ccaaggctcg agggcggcgg agagggcaga   2040
ggaagtcttc taacatgcgg tgacgtggag gagaatcccg ccctaggat gcttctcctg   2100 gtgacaagcc ttctgctctg tgagttacca cacccagcat tcctcctgat cccacgcaaa   2160
gtgtgtaacg aataggtat tggtgaattt aaagactcac tctccataaa tgctacgaat   2220
attaaacact tcaaaaactg cacctccatc agtggcgatc tccacatcct gccggtggca   2280
tttaggggtg actccttcac acatactcct cctctggatc cacaggaact ggatattctg   2340
aaaaccgtaa aggaaatcac agggtttttg ctgattcagg cttggcctga aaacaggacg   2400
gacctccatg cctttgagaa cctagaaatc atacgcggca ggaccaagca acatggtcag   2460
ttttctcttg cagtcgtcag cctgaacata acatccttgg gattacgctc cctcaaggag   2520
ataagtgatg gagatgtgat aatttcagga aacaaaaatt gtgctatgc aaatacaata   2580 aactggaaaa aactgtttgg gacctccggt cagaaaacca aaattataag caacagaggt   2640
gaaaacagct gcaaggccac aggccaggtc tgccatgcct gtgctcccc cgagggctgc   2700 tggggcccgg agcccaggga ctgcgtctct tgccggaatg tcagccgagg cagggaatgc   2760
gtggacaagt gcaaccttct ggagggtgag ccaagggagt tgtggagaa ctctgagtgc   2820 atacagtgcc acccagagtg cctgcctcag gccatgaaca tcacctgcac aggacgggga   2880
ccagacaact gtatccagtg tgcccactac attgacggcc cccactgcgt caagacctgc   2940
ccggcaggag tcatgggaga aaacaacacc ctggtctgga gtacgcaga cgccggccat   3000 gtgtgccacc tgtgccatcc aaactgcacc tacggatgca ctgggccagg tcttgaaggc   3060
tgtccaacga atgggcctaa gatcccgtcc atcgccactg ggatggtggg ggccctcctc   3120
ttgctgctgg tggtggccct ggggatcggc ctcttcatgt ga                     3162
```

<210> SEQ ID NO 38
<211> LENGTH: 1053
<212> TYPE: PRT
<213> ORGANISM: Artificial Sequence
<220> FEATURE:
<223> OTHER INFORMATION: CD33 EQ CAR preceded by a GMCSR signal sequence
       and followed by a T2A skip sequence and EGFRt

<400> SEQUENCE: 38

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

-continued

```
Val Lys Lys Pro Gly Ser Ser Val Lys Val Ser Cys Lys Ala Ser Gly
         35              40              45

Tyr Thr Phe Thr Asp Tyr Asn Met His Trp Val Arg Gln Ala Pro Gly
         50              55              60

Gln Gly Leu Glu Trp Ile Gly Tyr Ile Tyr Pro Tyr Asn Gly Gly Thr
65              70              75              80

Gly Tyr Asn Gln Lys Phe Lys Ser Lys Ala Thr Ile Thr Ala Asp Glu
             85              90              95

Ser Thr Asn Thr Ala Tyr Met Glu Leu Ser Ser Leu Arg Ser Glu Asp
             100             105             110

Thr Ala Val Tyr Tyr Cys Ala Arg Gly Arg Pro Ala Met Asp Tyr Trp
         115             120             125

Gly Gln Gly Thr Leu Val Thr Val Ser Ser Gly Gly Gly Ser Gly
    130             135             140

Gly Gly Gly Ser Gly Gly Gly Ser Asp Ile Gln Met Thr Gln Ser
145             150             155             160

Pro Ser Ser Leu Ser Ala Ser Val Gly Asp Arg Val Thr Ile Thr Cys
             165             170             175

Arg Ala Ser Glu Ser Val Asp Asn Tyr Gly Ile Ser Phe Met Asn Trp
             180             185             190

Phe Gln Gln Lys Pro Gly Lys Ala Pro Lys Leu Leu Ile Tyr Ala Ala
         195             200             205

Ser Asn Gln Gly Ser Gly Val Pro Ser Arg Phe Ser Gly Ser Gly Ser
    210             215             220

Gly Thr Asp Phe Thr Leu Thr Ile Ser Ser Leu Gln Pro Asp Asp Phe
225             230             235             240

Ala Thr Tyr Tyr Cys Gln Gln Ser Lys Glu Val Pro Trp Thr Phe Gly
             245             250             255

Gln Gly Thr Lys Val Glu Ile Lys Glu Ser Lys Tyr Gly Pro Pro Cys
         260             265             270

Pro Pro Cys Pro Ala Pro Glu Phe Glu Gly Gly Pro Ser Val Phe Leu
         275             280             285

Phe Pro Pro Lys Pro Lys Asp Thr Leu Met Ile Ser Arg Thr Pro Glu
    290             295             300

Val Thr Cys Val Val Val Asp Val Ser Gln Glu Asp Pro Glu Val Gln
305             310             315             320

Phe Asn Trp Tyr Val Asp Gly Val Glu Val His Asn Ala Lys Thr Lys
             325             330             335

Pro Arg Glu Glu Gln Phe Gln Ser Thr Tyr Arg Val Val Ser Val Leu
         340             345             350

Thr Val Leu His Gln Asp Trp Leu Asn Gly Lys Glu Tyr Lys Cys Lys
         355             360             365

Val Ser Asn Lys Gly Leu Pro Ser Ser Ile Glu Lys Thr Ile Ser Lys
    370             375             380

Ala Lys Gly Gln Pro Arg Glu Pro Gln Val Tyr Thr Leu Pro Pro Ser
385             390             395             400

Gln Glu Glu Met Thr Lys Asn Gln Val Ser Leu Thr Cys Leu Val Lys
             405             410             415

Gly Phe Tyr Pro Ser Asp Ile Ala Val Glu Trp Glu Ser Asn Gly Gln
         420             425             430

Pro Glu Asn Asn Tyr Lys Thr Thr Pro Pro Val Leu Asp Ser Asp Gly
         435             440             445
```

-continued

```
Ser Phe Phe Leu Tyr Ser Arg Leu Thr Val Asp Lys Ser Arg Trp Gln
    450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Met Ala Leu
                485                 490                 495

Ile Val Leu Gly Gly Val Ala Gly Leu Leu Leu Phe Ile Gly Leu Gly
                500                 505                 510

Ile Phe Phe Lys Arg Gly Arg Lys Lys Leu Leu Tyr Ile Phe Lys Gln
                515                 520                 525

Pro Phe Met Arg Pro Val Gln Thr Thr Gln Glu Glu Asp Gly Cys Ser
    530                 535                 540

Cys Arg Phe Pro Glu Glu Glu Glu Gly Gly Cys Glu Leu Gly Gly Gly
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
                580                 585                 590

Asp Val Leu Asp Lys Arg Arg Gly Arg Asp Pro Glu Met Gly Gly Lys
                595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
                660                 665                 670

Leu Glu Gly Gly Gly Glu Gly Arg Gly Ser Leu Leu Thr Cys Gly Asp
                675                 680                 685

Val Glu Glu Asn Pro Gly Pro Arg Met Leu Leu Leu Val Thr Ser Leu
    690                 695                 700

Leu Leu Cys Glu Leu Pro His Pro Ala Phe Leu Leu Ile Pro Arg Lys
705                 710                 715                 720

Val Cys Asn Gly Ile Gly Ile Gly Glu Phe Lys Asp Ser Leu Ser Ile
                725                 730                 735

Asn Ala Thr Asn Ile Lys His Phe Lys Asn Cys Thr Ser Ile Ser Gly
                740                 745                 750

Asp Leu His Ile Leu Pro Val Ala Phe Arg Gly Asp Ser Phe Thr His
                755                 760                 765

Thr Pro Pro Leu Asp Pro Gln Glu Leu Asp Ile Leu Lys Thr Val Lys
    770                 775                 780

Glu Ile Thr Gly Phe Leu Leu Ile Gln Ala Trp Pro Glu Asn Arg Thr
785                 790                 795                 800

Asp Leu His Ala Phe Glu Asn Leu Glu Ile Ile Arg Gly Arg Thr Lys
                805                 810                 815

Gln His Gly Gln Phe Ser Leu Ala Val Val Ser Leu Asn Ile Thr Ser
                820                 825                 830

Leu Gly Leu Arg Ser Leu Lys Glu Ile Ser Asp Gly Asp Val Ile Ile
                835                 840                 845

Ser Gly Asn Lys Asn Leu Cys Tyr Ala Asn Thr Ile Asn Trp Lys Lys
    850                 855                 860
```

-continued

```
Leu Phe Gly Thr Ser Gly Gln Lys Thr Lys Ile Ile Ser Asn Arg Gly
865             870             875             880

Glu Asn Ser Cys Lys Ala Thr Gly Gln Val Cys His Ala Leu Cys Ser
                885             890             895

Pro Glu Gly Cys Trp Gly Pro Glu Pro Arg Asp Cys Val Ser Cys Arg
                900             905             910

Asn Val Ser Arg Gly Arg Glu Cys Val Asp Lys Cys Asn Leu Leu Glu
            915             920             925

Gly Glu Pro Arg Glu Phe Val Glu Asn Ser Glu Cys Ile Gln Cys His
    930             935             940

Pro Glu Cys Leu Pro Gln Ala Met Asn Ile Thr Cys Thr Gly Arg Gly
945             950             955             960

Pro Asp Asn Cys Ile Gln Cys Ala His Tyr Ile Asp Gly Pro His Cys
                965             970             975

Val Lys Thr Cys Pro Ala Gly Val Met Gly Glu Asn Asn Thr Leu Val
                980             985             990

Trp Lys Tyr Ala Asp Ala Gly His Val Cys His Leu Cys His Pro Asn
            995             1000            1005

Cys Thr Tyr Gly Cys Thr Gly Pro Gly Leu Glu Gly Cys Pro Thr
    1010            1015            1020

Asn Gly Pro Lys Ile Pro Ser Ile Ala Thr Gly Met Val Gly Ala
    1025            1030            1035

Leu Leu Leu Leu Leu Val Val Ala Leu Gly Ile Gly Leu Phe Met
    1040            1045            1050
```